US006447539B1

(12) United States Patent
Nelson et al.

(10) Patent No.: US 6,447,539 B1
(45) Date of Patent: *Sep. 10, 2002

(54) METHOD AND APPARATUS FOR TREATING ISCHEMIC HEART DISEASE BY PROVIDING TRANSVENOUS MYOCARDIAL PERFUSION

(75) Inventors: James A. Nelson, Seattle; Ascher Shmulewitz, Mercer Island, both of WA (US); John Burton, Minnetonka, MN (US)

(73) Assignee: TransVascular, Inc., Menlo Park, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/929,076

(22) Filed: Sep. 15, 1997

Related U.S. Application Data

(60) Continuation-in-part of application No. 08/798,700, filed on Feb. 12, 1997, now Pat. No. 5,824,071, which is a division of application No. 08/714,466, filed on Sep. 16, 1996, now Pat. No. 5,655,548.

(51) Int. Cl.$^7$ .................................................. A61F 2/06
(52) U.S. Cl. ...................... 623/1.11; 128/898; 606/194; 604/93.01
(58) Field of Search .................. 128/898; 604/49, 604/96, 7–9, 93.01, 916; 606/194; 623/3, 1.1, 1.11, 11, 900; 600/16

(56) References Cited

U.S. PATENT DOCUMENTS

| 4,712,551 A | * 12/1987 | Rayhanabad .................. 604/8 |
| 5,287,861 A | 2/1994 | Wilk |

(List continued on next page.)

FOREIGN PATENT DOCUMENTS

| WO | WO97/13463 | 4/1997 |
| WO | WO97/13471 | 4/1997 |

(List continued on next page.)

OTHER PUBLICATIONS

U.S. Prov. appl. 60/028,922, Aug. 1996, Makower et al.
Mohl, Werner, "Coronary Sinus Interventions: From Concept to Clinics," *Journal of Cardiac Surgery*, vol. 2, No. 4, (Dec. 1987), pp. 467–493.
*Cardiac Catheterization and Angiography*, William Grossman, Ed., Lea & Febiger, Philadelphia (1980), pp. 63–69.

(List continued on next page.)

*Primary Examiner*—Vincent Millin
*Assistant Examiner*—Kelly Scaggs
(74) *Attorney, Agent, or Firm*—Robert Buyan; Stout, Uxa, Buyan & Mullins, LLP

(57) ABSTRACT

Methods and apparatus are provided for use in intraoperative and percutaneous procedures for supplying long-term retrograde perfusion of the myocardium via one or more conduits disposed between the left ventricle and the coronary venous vasculature. The conduits are of a selected size and number, and portions of the venous vasculature or coronary ostium are partially or completely occluded, to maintain a parameter related to the pressure attained in the venous vasculature to a value less than a predetermined value.

26 Claims, 10 Drawing Sheets

U.S. PATENT DOCUMENTS

| | | | |
|---|---|---|---|
| 5,380,316 A | 1/1995 | Aita et al. |
| 5,389,096 A | 2/1995 | Aita et al. |
| 5,409,019 A | 4/1995 | Wilk |
| 5,429,144 A | 7/1995 | Wilk |
| 5,549,581 A | 8/1996 | Lurie et al. |
| 5,830,222 A | 11/1998 | Makower et al. |

FOREIGN PATENT DOCUMENTS

| | | |
|---|---|---|
| WO | 98/06356 | 2/1998 |
| WO | 98/08456 | 3/1998 |
| WO | 98/46115 | 10/1998 |
| WO | 99/36000 | 7/1999 |
| WO | 99/36001 | 7/1999 |
| WO | 99/53863 | 10/1999 |

OTHER PUBLICATIONS

Ihnken, Kai et al., "The Safety of Simultaneous Arterial and Coronary Sinus Perfusion: Experimental Background and Initial Clinical Results," *Journal of Cardiac Surgery*, vol. 9, No. 1, (Jan. 1994), pp. 15–25.

Ihnken, Kai et al., "Simultaneous Arterial and Coronary Sinus Cardioplegic Perfusion: an Experimental and Clinical Study," *The Thoracic and Cardiovascular Surgeon*, vol. 42, (Jun. 1994), pp. 141–147.

Iguidbashian, John P. et al., "Advantages of Continuous Noncardioplegic Warm Blood Retrograde Perfusion over Antegrade Perfusion During Proximal Coronary Anastomoses," *Journal of Cardiac Surgery*, vol. 10, No. 1, (Jan. 1995), pp. 27–31.

Lichtenstein, Samuel V. et al., "Warm Retrograde Cardioplegia: Protection of the Right Ventrical in Mitral Valve Operations," *The Journal of Thoracic and Cardiovascular Surgery*, vol. 104, No. 2 ,(Aug. 1992), pp. 374–380.

Ropchan, Glorianne V. et al., "Salvage of Ischemic Myocardium by Nonsynchronized Retroperfusion in the Pig," *The Journal of Thoracic and Cardiovascular Surgery*, vol. 104, No. 3, (Sep. 1992), pp. 619–625.

Franz, N. et al., "Transfemoral Balloon Occlusion of the Coronary Sinus in Patients with Angina Pectoris," *Radiologia Diagnostica*, 31(1), (1990), pp. 35–41. (Abstract).

Kuraoka, S. et al., "Antegrade or Retrograde Blood Cardioplegic Method: Comparison of Postsurgical Right Ventricular Function and Conduction Disturbances," *Japanese Journal of Thoracic Surgery*, 48(5), (May 1995), pp. 383–386. (Abstract).

Lincoff, A.M. et al., "Percutaneous Support Devices for High Risk or Complicated Coronary Angioplasty," *Journal of the American College of Cardiology*, 17(3), (Mar. 1991), pp. 770–780.

Rudis, E. et al., "Coronary Sinus Ostial Occlusion During Retrograde Delivery of Cardioplegic Solution Significantly Improves Cardioplegic Distribution and Efficacy," *Journal of Thoracic and Cardiovascular Surgery*, 109(5), (May 1995), pp. 941–946.

Huang, A.H. et al., "Coronary Sinus Pressure and Arterial Venting Do Not Affect Retrograde Cardioplegia Distribution," *Annals of Thoracic Surgery*, 58(5), (Nov. 1994), pp. 1499–1504.

Tokunaga, S., et al., "Left Ventricular–Coronary Sinus Shunt Through a Septal Aneurysm After Mitral Valve Replacement," Annals of Thoracic Surgery, 59(1), (Jan. 1995), pp. 224–227.

\* cited by examiner

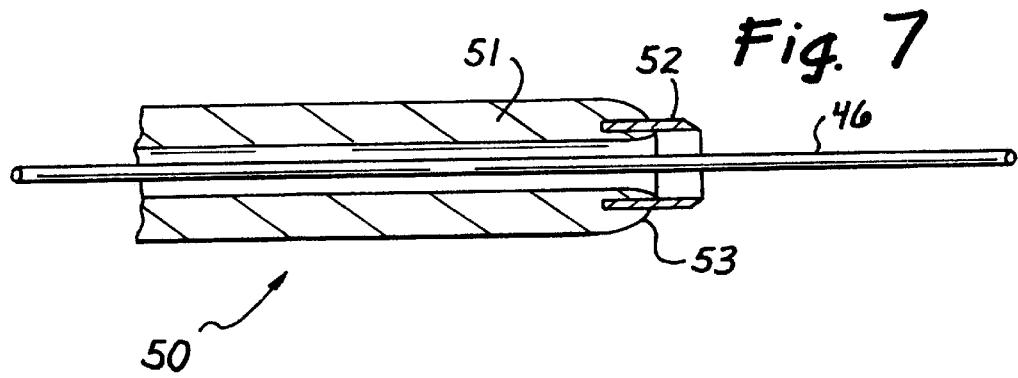
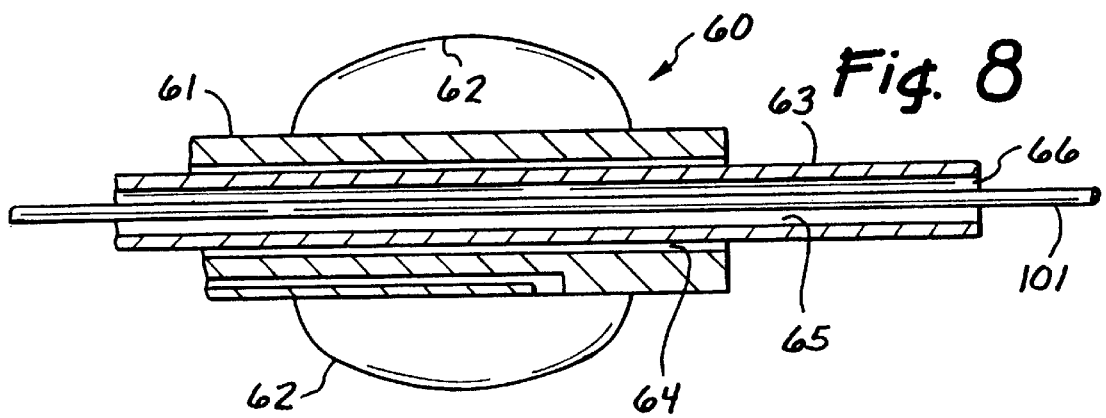
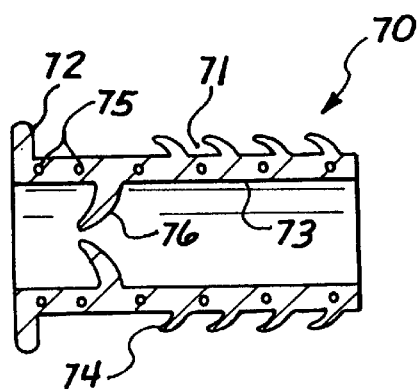
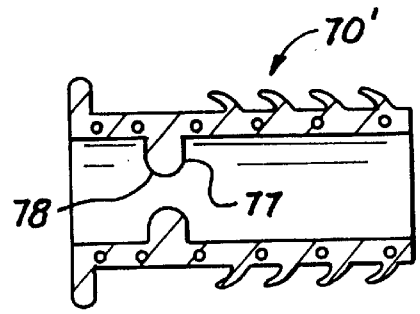
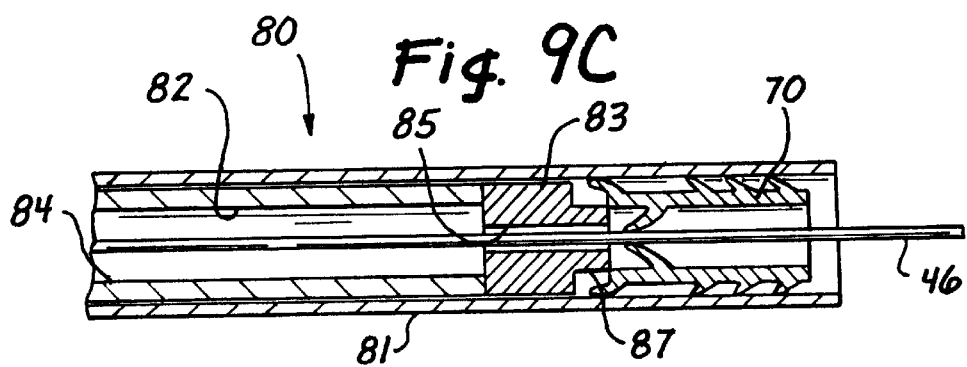

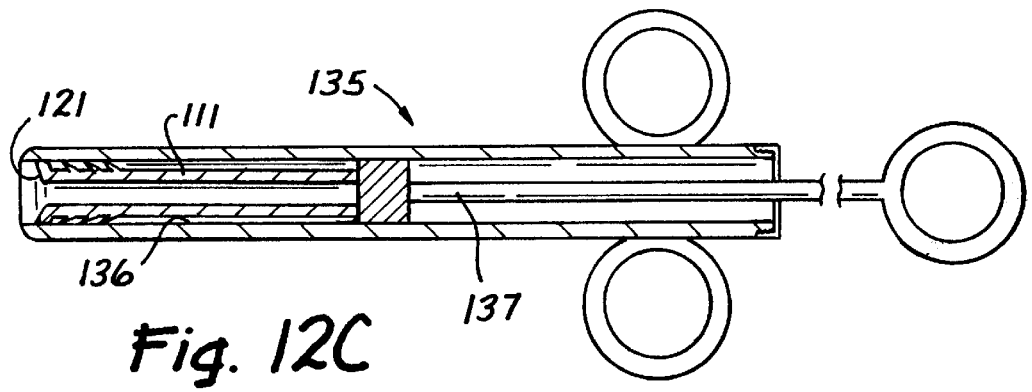
Fig. 12C
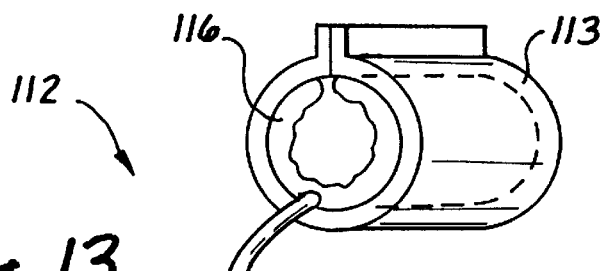
Fig. 13
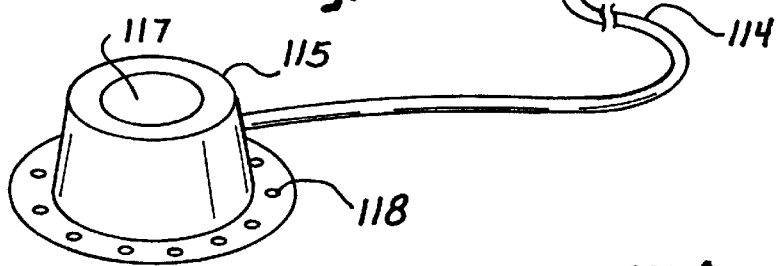
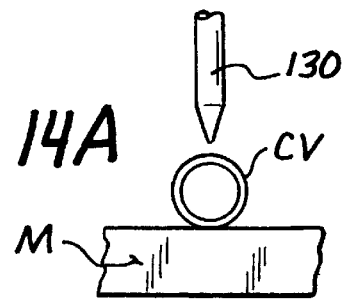
Fig. 14A
Fig. 14B
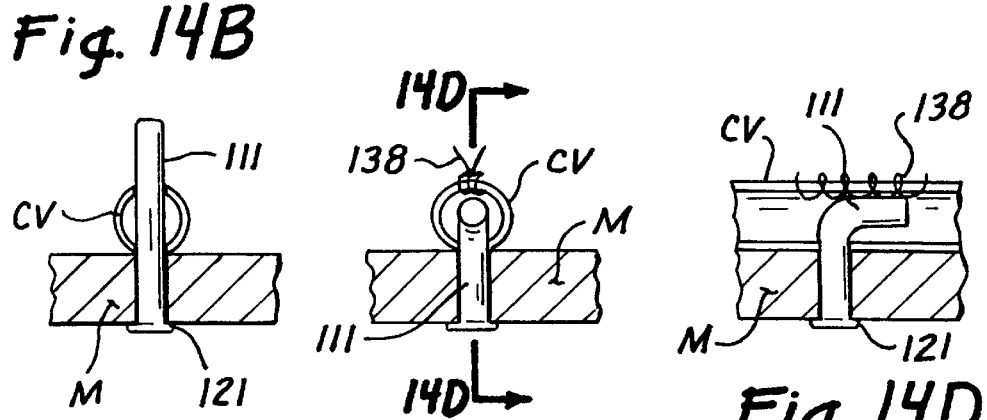
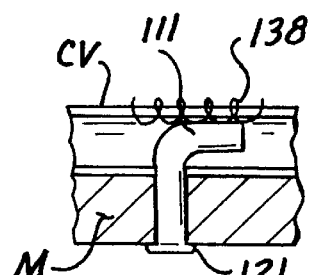
Fig. 14C
Fig. 14D

METHOD AND APPARATUS FOR TREATING ISCHEMIC HEART DISEASE BY PROVIDING TRANSVENOUS MYOCARDIAL PERFUSION

REFERENCE TO RELATED APPLICATIONS

This application is a continuation-in-part of U.S. patent application Ser. No. 08/798,700, filed Feb. 12, 1997, now U.S. Pat. No. 5,824,071 which is a division of U.S. patent application Ser. No. 08/714,466, filed Sep. 16, 1996, now U.S. Pat. No. 5,655,548.

FIELD OF THE INVENTION

The present invention relates generally to methods and apparatus for treating ischemic heart disease, and more particularly, cases involving diffuse coronary atherosclerosis, by perfusing the myocardium with oxygenated blood from the left ventricle using the coronary venous vasculature.

BACKGROUND OF THE INVENTION

The cardiac blood perfusion system is composed of two coronary arterial vessels, the left and right coronary arteries, which perfuse the myocardium from the epicardial surface inward towards the endocardium. Blood flows through the capillary systems into the coronary veins, and into the right atrium via the coronary sinus. Two additional systems, the lymphatic and the Thebesian veins, drain a portion of the blood perfused into the myocardium directly into the heart chambers. The venous system has extensive collaterals and, unlike the coronary arteries, does not occlude in atherosclerotic disease.

A number of techniques have been developed to treat ischemic heart disease caused, for example, by atherosclerosis. These treatments have improved the lives of millions of patients worldwide, yet for certain classes of patients current technology offers little relief or hope.

Best known of the current techniques is coronary artery bypass grafting, wherein a thoracotomy is performed to expose the patient's heart, and one or more coronary arteries are replaced with saphenous veins. In preparation for the bypass grafting, the heart is arrested using a suitable cardioplegia solution, while the patient is placed on cardiopulmonary bypass (i.e., a heart-lung machine) to maintain circulation throughout the body during the operation. Typically, a state of hypothermia is induced in the heart muscle during the bypass operation to reduce oxygen utilization, thereby preserving the tissue from further necrosis. Alternatively, the heart may be perfused throughout the operation using either normal or retrograde flow through the coronary sinus, with or without hypothermia. Once the bypass grafts are implanted, the heart is resuscitated, and the patient is removed from cardiopulmonary bypass.

Drawbacks of conventional open heart surgery are that such surgery is time-consuming and costly, involves a significant risk of mortality, requires a lengthy period of recuperation, and involves significant discomfort to the patient.

As a result of the foregoing drawbacks, techniques have been developed that permit coronary bypass grafting to be performed endoscopically, i.e., using elongated instruments inserted through incisions located between the ribs. A drawback of these keyhole techniques, however, is that they can be used only for coronary arteries that are readily accessible, and not, for example, those located posteriorly.

Alternatively, techniques such as percutaneous transluminal angioplasty ("PTA") have been developed for reopening arteries, such as the coronary arteries, that have become constricted by plaque. In these techniques, a balloon catheter is typically inserted into the stenosis and then inflated to compress and crack the plaque lining the vessel, thereby restoring patency to the vessel. Additionally, a vascular prosthesis, commonly referred to as a "stent," may be inserted transluminally and expanded within the vessel after the angioplasty procedure, to maintain the patency of the vessel after the PTA procedure.

U.S. Pat. No. 5,409,019 to Wilk describes an alternative method of creating a coronary bypass, wherein a valve-like stent is implanted within an opening formed between a coronary artery and the left ventricle. The patent describes that the stent may be implanted transluminally.

A drawback of the foregoing transluminal approaches is that the treatment device, e.g., the balloon catheter or the stent delivery system described in U.S. Pat. No. 5,409,019, must be inserted in the vessel before it can be expanded. Occasionally, a stenosis may occlude so much of a vessel that there is insufficient clearance to advance a guidewire and catheter within the stenosis to permit treatment. In addition, arterial blockages treatable using PTA techniques are restricted to the portions of the anatomy where such techniques can be beneficially employed.

Moreover, the above-described techniques—both open—surgery and transluminal—are useful only where the stenosis is localized, so that the bypass graft or PTA procedure, when completed, will restore near normal blood flow to the effected areas. For certain conditions, however, such as diffuse atherosclerosis, blockages may exist throughout much of the coronary artery system. In such situations, treatment, if possible, typically involves heart transplant.

Historically, attempts have been made to treat diffuse blockages of the coronary arterial system by introducing retrograde flow through the coronary venous system. As described, for example, in W. Mohl, "Coronary Sinus Interventions: From Concept to Clinics," *J. Cardiac Sura.*, Vol. 2, pp. 467–493 (1987), coronary venous bypass grafts have been attempted wherein the coronary sinus was ligated, and a shunt was implanted between a cardiac vein and the aorta, thus providing permanent retrograde perfusion. It was observed that such bypass grafts resulted in underperfusion of certain regions of the myocardium and edema of the venous system. Consequently, as reported in the aforementioned Mohl article, these techniques are rarely used in cardiac surgery, while permanent retroperfusion is never used in interventional cardiology.

Despite disenchantment with retroperfusion via the coronary sinus for long-term perfusion of the myocardium, retrograde coronary venous perfusion is now routinely used in coronary interventional procedures to perfuse the heart during the procedure. Franz et al., in "Transfemoral Balloon Occlusion of the Coronary Sinus in Patients with Angina Pectoris," *Radiologia Diagnostica*, 31(1), pp. 35–41 (1990), demonstrated the possibility of transfemoral coronary sinus balloon occlusion in patients with angina pectoris. In recent years, the use of retrograde arterial perfusion of blood through the coronary sinus has gained wide acceptance as a technique to preserve the myocardium during bypass procedures (Kuraoka et al., "Antegrade or Retrograde Blood Cardioplegic Method: Comparison of Post-Surgical Right Ventricular Function and Conduction Disturbances," *Japanese J. Thoracic Surg.*, 48(5), pp. 383–6, (1995)) and during high risk or complicated angioplasty (Lincoff et al., "Percutaneous Support Devices for High Risk or Complicated Coronary Angioplasty," *J. Am. Coll. Cardiol.*, 17(3), pp. 770–780 (1991)). This perfusion technique allows continuous warm cardioplegia and allows the flow of blood through the coronary venous bed distal to the occlusion.

It has also been reported by Rudis et al. in "Coronary Sinus Ostial Occlusion During Retrograde Delivery of Cardioplegic Solution Significantly Improves Cardioplegic Distribution and Efficiency," *J. Thoracic & Cardiovasc. Surg.*, 109(5), pp. 941–946 (1995), that retrograde blood flow through the coronary venous system may be augmented by coronary ostial occlusion. In this case, blood flows retrograde to the myocardium and drainage is through the lymphatic system and the Thebesian veins. Huang et al., in "Coronary Sinus Pressure and Arterial Venting Do Not Affect Retrograde Cardioplegic Distribution," *Annals Thoracin Surg.*, 58(5), pp. 1499–1504, that flow through the myocardium is not significantly effected by coronary arterial occlusion and venting, or by increases in coronary perfusion pressure. Also, K. Ihnken et al., in "Simultaneous Arterial and Coronary Sinus Cardioplegic Perfusion, an Experimental and Clinical Study," *Thoracic and Cardiovascular Surgeon*, Vol. 42, pp.141–147 (June 1994), demonstrated the benefits of using simultaneous arterial and coronary sinus perfusion during cardiac bypass surgery, with no ventricular edema, lactate production, lipid peroxidation, or effect on post-bypass left ventricular elastance or stroke work index.

For a large number of patients in the later phases of ischemic heart disease, and particularly diffuse atherosclerotic disease, current technology offers little relief or hope. In such instances, humanely extending the patient's life for additional months may provide significant physical and emotional benefits for the patient.

In view of the foregoing, it would be desirable to provide methods and apparatus for treating ischemic heart disease in a wider range of open surgical and interventional cardiology procedures.

It also would be desirable to provide methods and apparatus for providing transvenous myocardial perfusion that reduce the risk of edema within the venous system.

It would further be desirable to provide methods and apparatus that enable patients suffering from the later phases of diffuse ischemic heart disease to experience renewed vigor, reduced pain and improved emotional well-being during the final months or years of their lives.

SUMMARY OF THE INVENTION

In view of the foregoing, it is an object of this invention to provide methods and apparatus for treating ischemic heart disease in a wider range of open surgical and interventional cardiology procedures.

It is another object of the present invention to provide methods and apparatus for providing transvenous myocardial perfusion that reduce the risk of edema within the venous system.

It is a further object of this invention to provide methods and apparatus that enable patients suffering from the later phases of diffuse ischemic heart disease to experience renewed vigor, reduced pain and improved emotional well-being during the final months or years of their lives, or which provides critical time during which a donor heart, for example, may be located for transplantation.

In accordance with the present invention, methods and apparatus are provided for forming one or more passageways or conduits between the left ventricle and the coronary venous vasculature (hereinafter referred to a "veno-ventricular passageways"), thereby supplying long-term retrograde perfusion of the myocardium.

A first embodiment of the apparatus, suitable for use in percutaneous applications, is advanced through the coronary ostium (in the right atrium) and positioned within a selected portion of the venous vasculature. Access to the right atrium may be established using either the subclavian veins and the superior vena cava or an approach through a femoral vein. Once one or more passageways of suitable size are formed between the left ventricle and selected portions of the venous system using the apparatus of the present invention. The coronary ostium is then partially or fully occluded with a plug or valve constructed in accordance with the present invention.

In accordance with the methods of the present invention, the degree of occlusion of the coronary ostium is selected to provide adequate back-pressure in the venous system, so that blood flowing into the venous system from the left ventricle flows in a retrograde direction to perfuse the myocardium. Alternatively, or in addition, a plug may be deployed to occlude a portion of a vein upstream of the outlet of a veno-ventricular passageway, to occlude collaterals adjacent to the passageway, or both.

Further in accordance with the methods of the present invention, the apparatus provides a diameter of the passageway, or a number of veno-ventricular passageways, so that a parameter associated with the pressure attained in the venous system does not exceed a predetermined value. Alternatively, or in addition, a flow-limiting stent or valve optionally may be deployed in the veno-ventricular passageway to prevent overpressure in the venous system.

A second embodiment of the apparatus provides for formation of the veno-ventricular passageways, and implantation of support devices in those passageways, using intraoperative techniques.

Further alternative embodiments of the apparatus of the present invention comprise conduits that may be implanted either transseptally or extracorporeally. A third embodiment of apparatus comprises a conduit that includes a first end, which is inserted transseptally through the right atrium and obliquely into the posterior septal endocardium of the left ventricle via the posterior pyramidal space, and a second end which is inserted into the coronary sinus via the coronary ostium in the right atrium. The conduit may optionally include means for maintaining a parameter associated with the pressure attained in the conduit and coronary venous vasculature below a predetermined value, such as a one-way valve preventing backflow from the coronary sinus to the left ventricle during the late phases cardiac diastole.

A fourth embodiment of the invention, suitable for use in an intraoperative procedure, comprises a conduit having a first end that is affixed in communication with the left ventricle near its apex, and a second end having a plug that is inserted into the coronary ostium via an opening through the wall of the right atrium or vena cavae. In this embodiment, the mid-region of the conduit is disposed within the pericardium and may comprise an elastic material that assists in regulating the pressure of the blood flow entering the coronary sinus. The conduit may also include a tapered inlet that assists in regulating the flow.

Further features of the invention, its nature and various advantages will be more apparent from the accompanying drawings and the following detailed description of the preferred embodiments.

BRIEF DESCRIPTION OF THE DRAWINGS

FIG. 7 is a sectional view of an illustrative device for cutting a veno-ventricular passageway;

FIG. 8 is a sectional view of the distal end of a device for measuring pressure in the venous system and occluding the coronary ostium;

FIGS. 9A and 9B are sectional views of illustrative stents for regulating the flow of blood through a veno-ventricular passageway, while FIG. 9C is a sectional view of delivery device for implanting the stents of FIGS. 9A and 9B;

FIGS. 12A, 12B and 12C are, respectively, an illustrative veno-ventricular conduit, a cutting device and a conduit delivery device constructed in accordance with the present invention;

FIG. 13 is an illustrative embodiment of a device for selectively and adjustably constricting the coronary sinus;

FIGS. 14A to 14C depict the sequence of deploying the apparatus of FIGS. 12A and 13, while FIG. 14D shows the view taken along view line 14D—14D of FIG. 14C;

DETAILED DESCRIPTION OF THE INVENTION

The present invention relates generally to methods and apparatus for use in percutaneous and intraoperative procedures for providing transvenous myocardial perfusion for patients suffering from diffuse forms of ischemic heart disease, such as atherosclerosis. In accordance with the present invention, the apparatus forms a passageway or conduit between the left ventricle and the coronary venous vasculature (i.e., coronary sinus and connecting cardiac veins) to permit blood ejected from the left ventricle to enter the venous system and perfuse the myocardium. Hereinafter, such passageways or conduits are referred to as "veno-ventricular passageways."

Further in accordance with the methods and apparatus of the present invention, a parameter associated with the pressure attained in the venous system preferably is limited to a value less than a predetermined value. For example, the peak pressure attained in the venous system may be limited to a value less than that believed to result in edema, generally, about 60 mm Hg.

This description of the present invention is organized as follows: First, the anatomy of the heart and coronary venous system relevant to the present invention are described. A heart, illustratively treated with methods of, and apparatus constructed in accordance with, the present invention, is then described. This is followed by a description of the components of a first embodiment of the apparatus of the present invention and operation thereof. Use of the apparatus in accordance with the methods of the present invention is described. Finally, alternative embodiments of the apparatus of the present invention are described, together with methods of employing that apparatus.

Figure 1A:
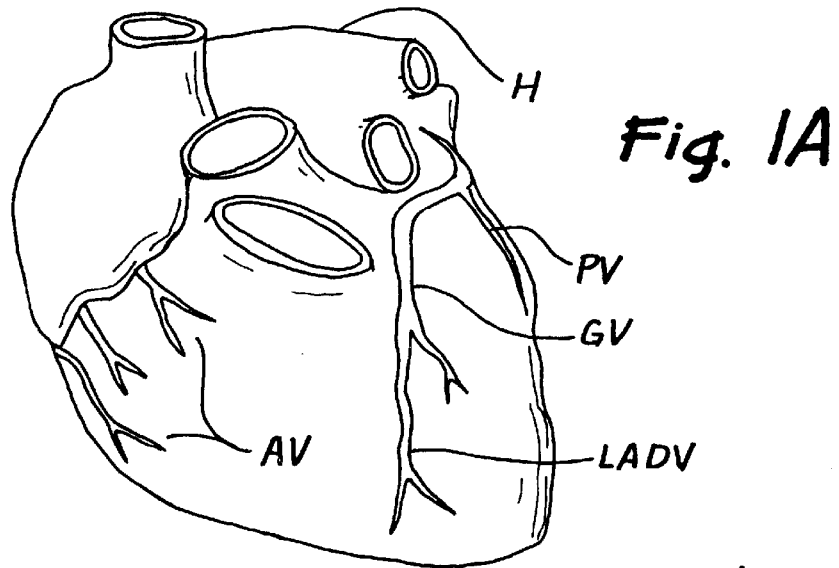
FIGS. 1A and 1B are partial sternocoastal and diaphragmatic surface views of a human heart illustrating the coronary venous vasculature.
Figure 1B:
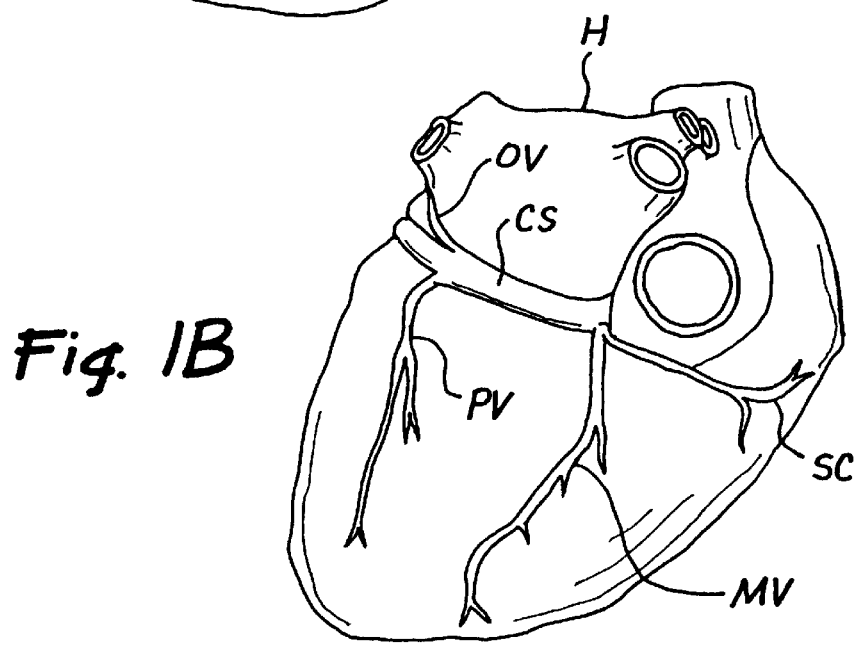
Figure 2:
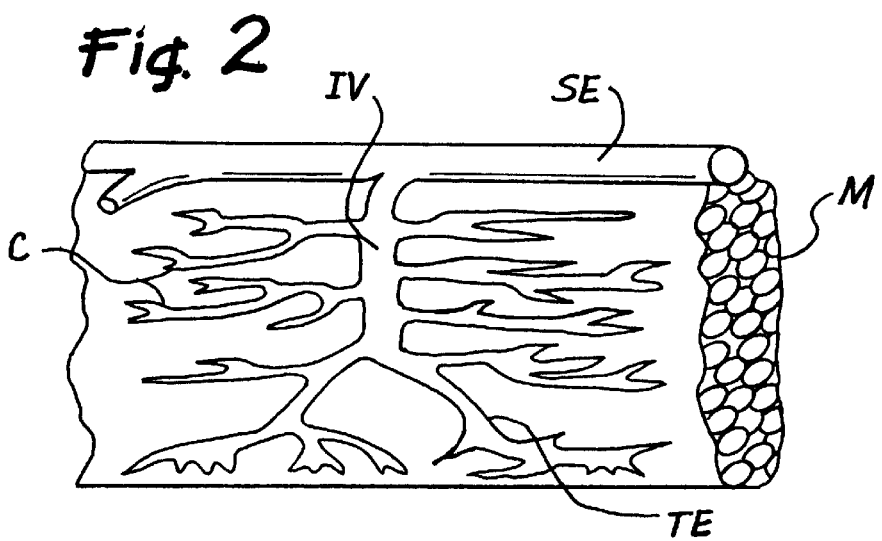
FIG. 2 is a sectional view of the myocardium, showing certain components of the cardiac venous system.

Referring to FIGS. 1A, 1B and 2, the coronary venous vasculature of human heart H and a model of the myocardial veins, respectively, are described. The venous system comprises coronary sinus CS that provides drainage for great cardiac vein GV, left anterior descending cardiac vein LADV, middle cardiac vein MV, the oblique vein of the left atrium OV, the posterior vein of the left ventricle PV and small cardiac vein SC. Deoxygenated blood flowing into coronary sinus CS exits via coronary ostium CO into the right atrium. The venous system further includes anterior cardiac veins AV that drain directly into the right atrium.

With respect to FIG. 2, myocardium M includes a lattice of capillaries C that drain deoxygenated blood into intramyocardial veins IV. From intramyocardial veins IV, a fraction of the blood drains into the cardiac veins via subepicardial veins SE, while the remainder drains through the Thebesian veins TE directly into the atrial and ventricular cavities. It has been reported in healthy human hearts that approximately 70% of the deoxygenated blood is drained through the coronary sinus, while the remaining 30% is drained in about equal proportions into the left and right atria and ventricles via the lymphatic system and the Thebesian veins. It has likewise been reported that when individual components of the venous system (i.e., the coronary sinus, lymphatic system and Thebesian veins) are occluded, the flow redistributes itself through the remaining unoccluded channels.

The coronary arteries are formed of resilient tissue fibers that withstand the pressures typically generated in the left ventricle during cardiac systole, generally up to a peak pressure of about 120 mm Hg. By contrast, the tissue fibers of the cardiac venous system are much less resilient than those of the coronary arterial system, with pressures in the coronary sinus generally not exceeding 6–10 mm Hg. Consequently, as reported in the aforementioned Mohl article, long-term retroperfusion via the coronary sinus can lead to edema of the cardiac veins, which are generally believed to be incapable of sustaining long-term pressures above about 60 mm Hg. The apparatus of the present invention are intended to address this significant drawback of long-term retroperfusion via the coronary venous system.

Figure 3:
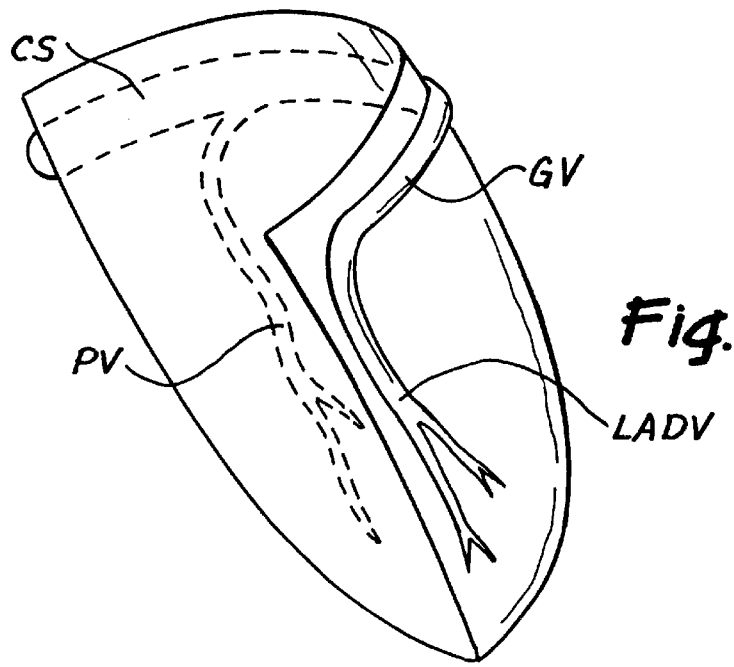
FIG. 3 is a perspective view from inside the left ventricle showing the spatial relationships between the portions of the coronary venous vasculature overlying the left ventricle.

In FIG. 3 the relative positions of portions of the coronary venous vasculature are shown with respect to the left ventricle, i.e., those vessels disposed on the epicardium directly overlying the left ventricle. More specifically, portions of the coronary sinus CS, the great cardiac vein GV, the left anterior descending cardiac vein LADV, and posterior vein of the left ventricle PV, overlie the left ventricle. The spatial relationships of the coronary sinus and veins depicted in FIG. 3 are intended to be merely illustrative, since normal hearts can show a considerable degree of variation.

The apparatus of the present invention is employed to form one or more veno-ventricular passageways through the myocardium between the left ventricle and the overlying portions of the venous vasculature depicted in FIG. 3. The passageways are cut by a device that preferably removes a core of tissue, so that the passageway is kept patent by flow passing therethrough. Alternatively, the passageway may be lined with a stent. In either case, the diameter of the passageway, or number of passageways, may be selected to ensure that certain criterion (e.g., a pressure parameter) attained in the venous system is less than some predetermined value.

Upon completion of the formation of the veno-ventricular passageways, a plug may be disposed in the coronary sinus to partially or completely occlude the coronary ostium. This plug is intended to create sufficient backpressure in the venous system that oxygenated blood ejected by the left ventricle into the venous system flows in a retrograde direction, thereby perfusing a portion of the myocardium. Alternatively, or in addition, segmental retroperfusion may be provided by occluding the cardiac vein just proximally of the veno-ventricular passageway (in the context of the cardiac veins, the proximal direction is closest to the coronary ostium).

Figure 4:
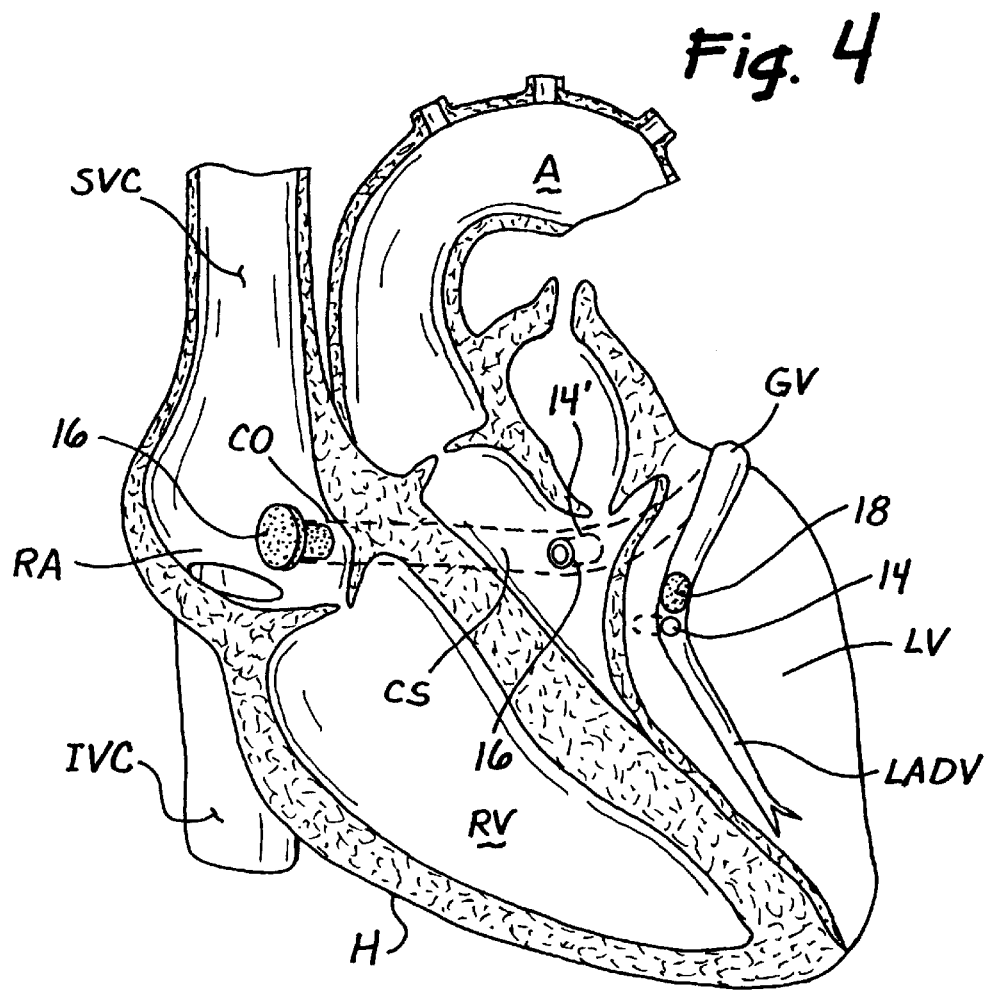
FIG. 4 is a view of a human heart, partly in section, treated methods and apparatus in accordance with a first embodiment of the present invention.

Referring now to FIG. 4, a human heart treated with the methods and apparatus of the present invention is described. FIG. 4 depicts human heart H partly in cross-section, within which apparatus of the present invention has been deployed in accordance with the methods described hereinafter. Human heart H includes superior vena cava SVC and inferior vena cava IVC communicating with right atrium RA, right ventricle RV, left atrium LA, left ventricle LV, and aorta A (for clarity, the pulmonary artery has been omitted). From the posterior to anterior regions of the heart H, coronary sinus CS enters the right atrium RA via the coronary ostium CO, passes behind heart H (shown in dotted outline), and connects to great cardiac vein GV and left anterior descending vein LADV.

In FIG. 4, heart H is shown after completion of the treatment using the apparatus of the present invention. Heart H includes veno-ventricular passageway 14 formed between left ventricle LV and the left anterior descending cardiac vein LADV and veno-ventricular passageway 14' formed between the left ventricle and coronary sinus CS. Plug 16 is lodged in, and either partially, progressively, or fully, occludes coronary ostium CO. During cardiac systole and the early phases of cardiac diastole, blood is ejected through passageways 14 and 14' and into the respective portions of the venous vasculature where it perfuses a region of the myocardium. Passageway 14' is fitted with an optional flow-limiting stent 17, while left anterior descending cardiac vein LADV includes plug 18 disposed just proximally of the outlet of passageway 14, to segregate that portion of the vein from the great cardiac vein GV.

With respect to FIGS. 5 through 9, the components of the first embodiment of apparatus are now described. This apparatus generally includes: a plug for partially or completely occluding the coronary ostium or a segment of the venous vasculature (FIGS. 5A–5E); a device for placing a guidewire between the venous system and the left ventricle (FIG. 6); a series of devices for cutting a core of tissue of predetermined size to form the veno-ventricular passageways (FIG. 7); a device for optionally monitoring a pressure-related parameter in the venous system (FIG. 8); and an optional stent and delivery system for sizing and maintaining the patency of the veno-ventricular passageway (FIGS. 9A, 9B and 9C). In addition to the foregoing, certain additional components, such as previously known balloon catheters, may be advantageously employed in conjunction with the methods and apparatus of the invention, as described hereinbelow.

Figure 5A:
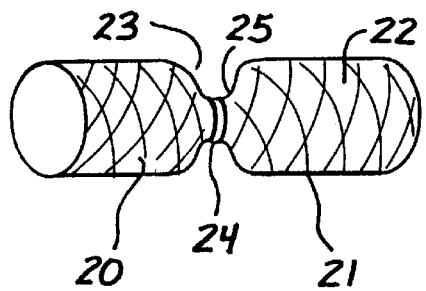
FIGS. 5A to 5E are illustrative embodiments of plugs for partially or fully occluding the coronary ostium or portions of the coronary vasculature.

Referring now to FIGS. 5A to 5D, four alternative embodiments of plug 12 constructed in accordance with the present invention are described. FIG. 5A depicts stent 20 of the type described in U.S. Pat. No. 4,655,771, commercially sold as the Wallstent®, available from Schneider (U.S.A.) Inc., Plymouth, Minnesota. Stent 20 comprises woven mesh structure 21 covered with polyurethane coating 22. Stent 20 assumes a reduced diameter when stretched longitudinally, and returns to its expanded diameter when the longitudinal restraint is removed.

In the context of the present invention, stent 20 is modified by wrapping mid-region 23 with suitable high strength wire 24, e.g., stainless steel, to form constriction 25. Thus, when stent 20 is delivered into the coronary sinus or a cardiac vein and the longitudinal restraint is removed, the ends of the stent expand into engagement with the walls of the vessel (as described in the above-incorporated U.S. Pat. No. 4,655,771), while mid-region 23 remains constricted. Depending upon how tightly mid-region 23 of stent 20 is constricted, the stent may be used either to partially or fully occlude a vessel.

Figure 5B:
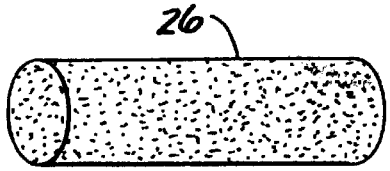

In FIG. 5B, an alternative embodiment of the plug comprises cylinder-26 of open-cell, high durometer, foam. The foam may be compressed and inserted within a sheath (not shown) for delivery into the coronary sinus or a cardiac vein. Once positioned in the vessel, the sheath is withdrawn, and the foam is permitted to resume its expanded shape. Because the foam has an open-cell structure, it is expected that initially some blood will pass through the structure. It is further expected, however, that over a period of time, e.g., a few hours, days, weeks or longer, the open-cell foam will clog and clot off, thereby progressively occluding the vessel. This is expected to provide a beneficial effect in that the heart has a period of time over which to accommodate the redistribution of flow, for example, through the lymphatic system and Thebesian veins.

Figure 5C:
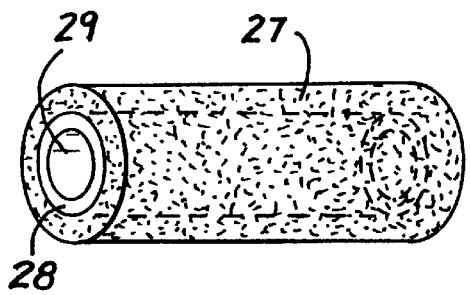

In FIG. 5C, another alternative embodiment of the plug is described, in which a layer of open-cell foam 27 of high durometer is affixed to the exterior of a previously known stent 28, such as those described in U.S. Pat. No. 4,733,665 to Palmaz or U.S. Pat. No. 5,443,500 to Sigwart et al. Stent 28 of FIG. 5C preferably is positioned in the coronary sinus or a cardiac vein, and then expanded by a conventional dilatation device (not shown) so that the open-cell foam 27 engages the wall of the vessel. Lumen 29 through the center of stent 28 may then be adjusted (either by permanent deformation in the Palmaz-type stent, or a ratcheting effect of the teeth in the Sigwart-type stent) to regulate the flow through the stent. Like the embodiment of FIG. 5B, foam portion 27 of the plug of FIG. 5C is expected to clot off after a period of time, thereby providing a gradual increase in the backpressure experienced in the venous system.

Figure 5D:
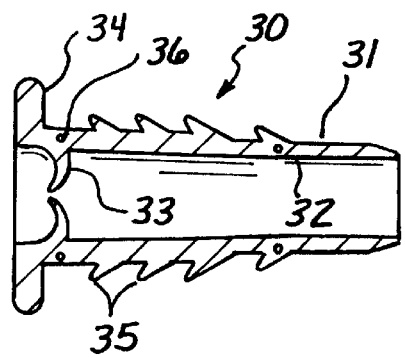

In FIG. 5D, plug 30 comprises a resilient biocompatible material, e.g., silicon or soft plastic, which is formed into a slightly tapered tubular member 31. Tubular member 31 includes bore 32 and pressure sensitive valve 33 disposed in bore 32. Tubular member 31 further includes proximal flange 34 that abuts against the right atrial endocardium and a plurality of resilient barbs or ribs 35 that engage the interior wall of the coronary sinus when plug 30 is disposed in coronary sinus CS through coronary ostium CO, thereby securing plug 30 in position. Plug 30 also may include radiopaque marker rings 36, e.g., gold hoops, embedded in the thickness of tubular member 31 for determining the location and orientation of plug 30 under fluoroscopic imaging.

Figure 5E:
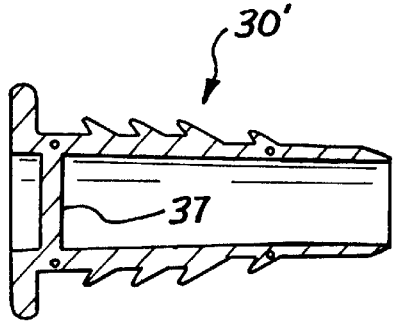

Pressure sensitive valve 33, for example, may be designed to remain closed until the pressure in the coronary sinus reaches about 60 mm Hg, and then open to vent any additional blood ejected into the venous system via the veno-ventricular passageway to be vented into right atrium RA. Pressure sensitive valve 33 may be constructed employing knowledge per se known in the art for construction of synthetic valves. Alternatively, as shown in FIG. 5E, plug 30' may include membrane 37. Membrane 37 completely occludes lumen 32, or may include a reduced diameter aperture (not shown), wherein the aperture lets sufficient quantities of blood be continuously vented into the right atrium to regulate the pressure in the venous system.

Figure 6:
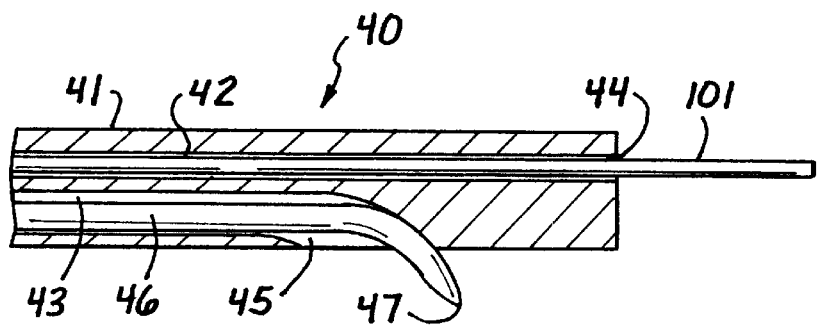
FIG. 6 is a sectional view of the distal end of a device for placing a guidewire between a portion of the coronary venous vasculature and the left ventricle.

Referring now to FIG. 6, the distal end of device 40 suitable for placing a guidewire from the venous system to the left ventricle is described. Device 40 comprises catheter 41 having lumens 42 and 43. Lumen 42 extends from the proximal end (i.e., outside the patient) to the distal end of the catheter, and includes outlet 44 in the distal endface of catheter 41. Lumen 42 accepts guidewire 101 along which catheter 41 may be advanced. Lumen 43 extends from the proximal end to the distal end of catheter, and exits through opening 45 in the lateral wall of catheter 41.

Device 40 is employed as follows: Once catheter 41 is positioned at a desired location in the venous system (i.e., the coronary sinus, great cardiac vein or other vein), guidewire 46 having sharpened tip 47 is advanced through lumen 43 so that tip 47 exits through opening 45, punctures the myocardium, and enters the left ventricle. Guidewire 46 is then advanced into the left ventricle to guide a cutting tool, described hereinafter, to core out a veno-ventricular passageway serve as a guide, or may be captured with a snare in the left ventricle and brought out via the aorta and femoral artery. Guidewire 46 is then retained in position while catheter 41 is withdrawn. Device 40 is preferably constructed of biocompatible materials typically employed in catheter construction, e.g., polyvinyl chloride or polyethylene.

In FIG. 7, the distal end of illustrative device 50 for cutting a passageway between the left ventricle and the coronary sinus or cardiac vein is described. Device 50 comprises catheter 51 having sharpened tubular member 52 of selected diameter affixed to distal end 53. Device 50 is advanced along guidewire 46 previously placed by device 40 (either from the ventricle side or the venous side), so that sharpened tubular member 52 is urged against the tissue, substantially transverse to the longitudinal orientation of catheter 51. Device 50 may then to urged distally, with or without manual rotation, to core out a passageway of predetermined size between the ventricle and the coronary sinus or cardiac vein.

It is expected that a parameter associated with the pressure attained in the venous system, caused by flow through the veno-ventricular passageway, may be controlled as a function of the diameter of the passageway, or number of passageways. This parameter may include, for example, peak pressure, mean pressure or rate of change of the pressure with respect to time (dP/dt). Accordingly, a variety of devices 50, each having a sharpened tubular member of different diameter, preferably are available to the clinician to cut the passageway to a desired size, as described hereinbelow. Alternatively, a series of adjacent passageways may be formed, and the flow thus controlled as a function of the cross-sectional area of the passageways.

Device 50 is merely illustrative of the kind of device which may be advantageously employed to form the veno-ventricular passageways, and other instruments including a distal end effector capable of penetrating the cardiac wall may be used. For example, device 50 may alternatively include laser cutting tip, as described, for example, in U.S. Pat. No. 5,104,393, which is incorporated herein by reference, or a mechanical cutting element, such as a rotating blade (commonly used in atherectomy)., or an RF ablation arrangement. Catheter 51 preferably comprises a biocompatible material typically employed in catheter construction, while the sharpened tubular member may comprise a metal or metal alloy, e.g., stainless steel.

In FIG. 8, the distal end of device 60 used in monitoring a parameter related to the pressure attained in the venous system in the vicinity of the veno-ventricular passageway is described. Device 60 includes outer catheter 61 carrying inflatable balloon 62. Inner catheter 63 is disposed in lumen 64 of outer catheter 61 for reciprocation therethrough, and includes pressure monitoring lumen 65 and port 66. Pressure monitoring lumen 65 is connected at its proximal end to a pressure transducer and pressure monitoring system, as are conventionally used in cardiac bypass surgery. The pressure monitoring system is preferably programmed to compute and display a parameter such as peak pressure, mean pressure, or dP/dt.

Operation of device 60 is as follows: device 60 is advanced along guidewire 101 from the venous side (i.e., through the coronary ostium) so that balloon 62 is disposed within the coronary sinus adjacent to the coronary ostium. Balloon 62 is then inflated to retain outer catheter 61 in position and occlude the coronary ostium. Inner catheter 63 is then advanced through outer catheter 61, and along guidewire 101, until pressure monitoring port 66 is disposed just adjacent to the veno-ventricular passageway. Device 60 may therefore be employed to monitor the pressure in the venous system just adjacent to the veno-ventricular passageway, and thereby ensure that the passageway is not cut to a diameter (or in numbers) at which the peak pressure (or some other relevant criterion) exceeds a predetermined value (e.g., 60 mm Hg).

Referring now to FIGS. 9A to 9C, optional stent 70 for use in sizing the diameter of a veno-ventricular passageway or maintaining the patency of the passageway is described. In one embodiment, stent 70 is preferably similar in design to plug 30, and includes tubular member 71 having proximal flange 72, bore 73 and resilient barbs or ribs 74 disposed around its circumference. Stent 70 preferably comprises a compliant material capable of bending along its length, such as silicon or a resilient plastic, thus permitting the stent to be transported transluminally through tortuous passages. Stent 70 also may have embedded within tubular member 71 circumferential hoops 75 formed of a relatively rigid material, e.g., stainless steel. Hoops 75, if provided, enable the stent to resist radial compression, thereby enabling stent 70 to maintain the patency of bore 73 against contraction of the left ventricular myocardium.

In accordance with the methods of the present invention, stent 70 may include valve 76 that prevents blood from being drawn from the venous system into the left ventricle during the later phases of cardiac diastole. Certain of hoops 75 also may be coated with a radiopaque material visible under fluoroscopic imaging. Proximal flange 72 abuts against the interior wall of the coronary sinus or cardiac vein when stent 70 is implanted in the veno-ventricular passageway. Barbs or ribs 74 secure the stent from being withdrawn into the venous system, while proximal flange 72 prevents the stent from being drawn into the left ventricle.

In an alternative embodiment of stent 70' shown in FIG. 9B, valve 76 is replaced by washer 77 having central aperture 78. Washer 77 preferably is available with a variety of apertures 78 having different diameters. In accordance with one aspect of the invention, the size of aperture 78 may be employed to regulate the parameter associated with the pressure attained in the venous system. In particular, applicants expect that by controlling the diameter of the aperture, the volume of blood ejected into the venous system may be regulated, and thus a pressure-related parameter for the pressure attained in the venous system may be kept below a predetermined value.

In FIG. 9C, an illustrative device 80 for delivering and implanting plug 30 and stent 70 are described. Device 80 includes exterior sheath 81, pusher member 82 disposed to reciprocate within exterior sheath 81 and spool 83 affixed to the distal end of pusher member 82. Pusher member 82 and spool 83 include central bores 84 and 85, respectively, through which guidewire 46 slidably extends. The distal end of spool 83 includes step 87 that is dimensioned to loosely engage bore 73 of stent 70.

Stent 70 is loaded into the distal end of catheter 80 within exterior sheath 81 so that flange 72 of the stent is flexibly bent longitudinally between spool 83 and exterior sheath 81, and step 87 loosely engages the proximal end of bore 73. Device 80 is advanced along guidewire 46 until it abuts against the wall of the coronary sinus or cardiac vein. Pusher member 82 is then advanced within exterior sheath 81 so that spool 83 urges stent 70 out of sheath 81 and, guided by guidewire 46, into engagement in the veno-ventricular passageway formed by device 50.

Stent 70 is intended to be merely illustrative to the types of devices that may be employed in practicing the present invention. Other types of stents, such as the coiled-sheet stent described in U.S. Pat. No. 5,443,500 to Sigwart also may be advantageously used to both size the veno-ventricular passageway and to kept it patent. The coiled sheet stent described in the above-mentioned Sigwart patent includes a plurality of locking teeth, which enable the stent to be expanded to a number of expanded diameters by selective inflation with a balloon dilatation device. In addition, because such stents are formed of a resilient material, they are expected to withstand crushing forces imposed during contraction of the myocardium.

As discussed hereinabove with respect to the plug for the coronary ostium (or cardiac vein), applicants expect that the one or more veno-ventricular passageways formed by, for example, device 50, will remain patent without the need for stent 70 or other means of lining the passageway. Thus, it is expected that by controlling the size to which the passageway is cut, a parameter associated with the pressure in the venous system may be maintained below a predetermined value.

Alternatively, the veno-ventricular passageways may be cut to a single predetermined size suitable for accepting stent 70 or a similar device. In this case flow through the passageway further may be controlled by selecting the aperture in the washer employed in stent 70, or by adjusting the degree of radial expansion of the coiled sheet stent using a dilatation device. Thus, the flow of blood from the left ventricle into the coronary sinus or cardiac vein (or veins), and hence the pressure profile developed in the venous system, may be controlled either by the size or number of the veno-ventricular passageways.

Figure 10A:
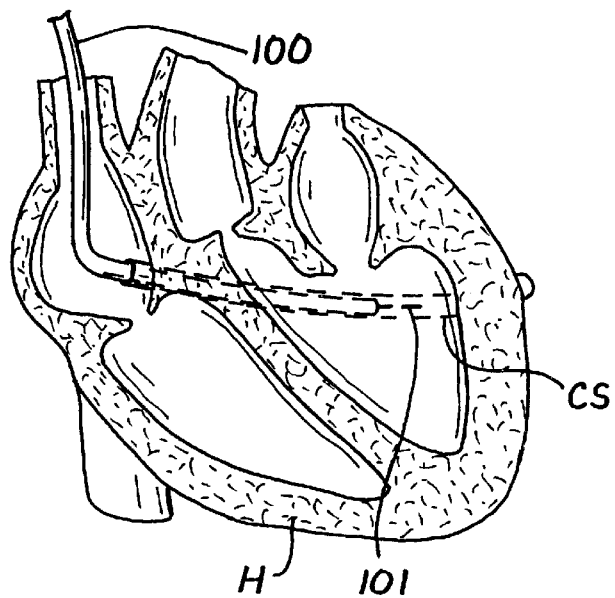
FIGS. 10A–10C illustrate the steps of transluminally providing venous retroperfusion in constructed in accordance with the methods of the present invention.
Figure 10B:
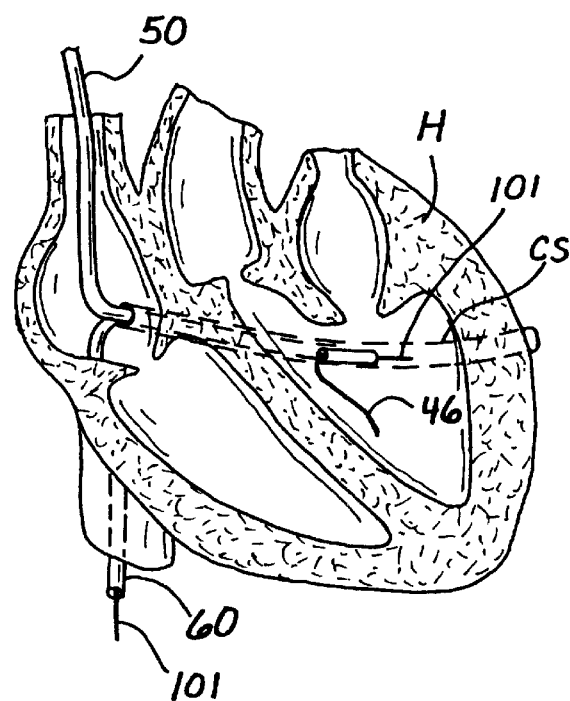
Figure 10C:
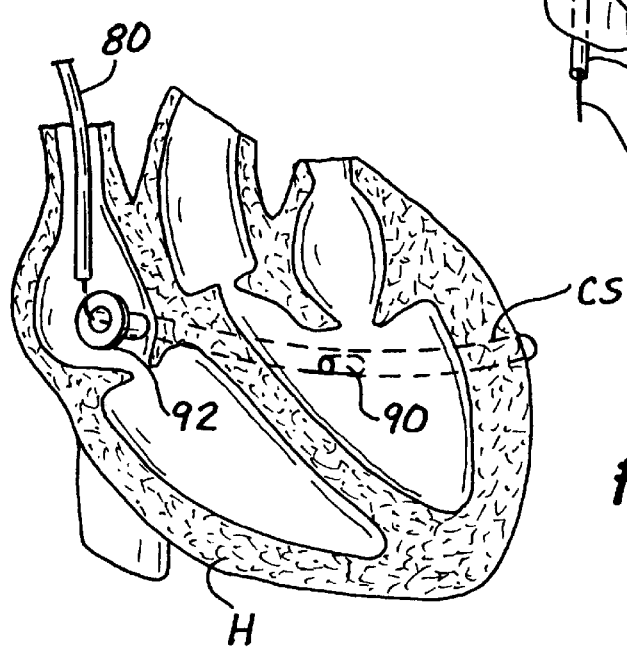

Referring now to FIGS. 10A to 10C, a method of the present invention for treating an ischemic heart using the first embodiment of apparatus of the present invention is described. Referring to FIG. 10A, device 100 is shown which preferably comprises a previously known catheter having distally located piezoelectric ultrasound elements for mapping the coronary venous vasculature and anatomy of the adjacent left ventricle. Device 100 is advanced along guidewire 101 through the axillary and subclavian veins (not shown) and into right atrium RA via superior vena cava SVC. Device 100 is then advanced through coronary ostium CO, through the coronary sinus CS, and into a desired cardiac vein, e.g., the posterior vein of the left ventricle PV. The signals generated by device 100 preferably are employed to map out the anatomy of all of the veins adjacent to the left ventricle. The precise spatial relationships between the coronary sinus, the cardiac veins and interior of the left ventricle may be ascertained, as illustrated, for example in FIG. 3.

Once the clinician has mapped the pertinent features of the heart, device 100 is withdrawn (with guidewire 101 is left in place) and device 40 of FIG. 6 is advanced along the guidewire, through the coronary ostium and into a selected portion of the venous system. If multiple veno-ventricular passageways are to be formed, as in FIG. 4, device 40 preferably is inserted to the distal-most portion of the venous vasculature first (i.e., that furthest away from the coronary ostium).

When device 40 is positioned at a desired location, for example, using fluoroscopy, guidewire 46 is advanced through lumen 43 of catheter 41 until sharpened tip 47 exits through opening 45 and punctures the wall of the vessel and the myocardium and enters the left ventricle. Guidewire 46 may then be further advanced to form a coil in the left ventricle or snared and brought out through the aorta and a femoral artery. Device 40 is removed, leaving guidewires 46 and 101 in position.

As illustrated in FIG. 10B, device 50 is advanced along guidewire 46 until the sharpened tubular member 52 is urged against the wall of the venous system. Device 60 may then be advanced along guidewire 101 so that balloon 62 is disposed in the coronary sinus. Balloon 62 (not visible in FIG. 10B) is inflated to partially or fully occlude the coronary ostium, and inner catheter 63, including pressure monitoring port 66, is advanced to a position just proximal of the distal end of device 50. Device 50 is then urged along guidewire 46, either with or without some rotational motion, to cut a core of myocardial tissue, thus forming venoventricular passageway 90.

When the core cut by device 50 is withdrawn, device 60 is employed to measure the increase in venous system pressure resulting from blood passing through the veno-ventricular passageway. If the diameter of the passageway is such that a pressure-related metric is far below a predetermined level, device 50 may be withdrawn along guidewire 46, and another device 50, capable of cutting a larger diameter core, may be used to enlarge the veno-ventricular-passageway. When the venous system pressure metric reaches an acceptable level (e.g, a peak pressure of 50 mm Hg), device 50 and guidewire 46 may be withdrawn. Balloon 62 is then deflated and withdrawn as well.

Alternatively, instead of enlarging the veno-ventricular passageway formed by device 50, devices 40 and 50 may be used repeatedly to create a plurality of adjacent holes in the same portion of the venous vasculature. In this manner, the cumulative flow area into the venous vasculature may be incrementally increased so the desired pressure-related parameter reaches, but does not exceed, the predetermined level.

If the clinician desires to employ retroperfusion in a segmental fashion, i.e., by breaking up the venous flow path into segments, a plug, such as shown in FIGS. 5A to 5C, may be deployed in the cardiac vein just proximal of the veno-ventricular passageway to partially or completely occlude the vein (see plug 18 of FIG. 4). In this manner, the clinician may ensure that blood flow into the vein through the veno-ventricular passageway will move in a retrograde fashion through that segment of the vein. In addition, to reduce the loss of retrograde flow through the collateral veins, as described hereinafter, the coronary ostium may be either partially or fully occluded as well, or progressively occluded using the plugs described with respect to FIGS. 5B and 5C.

At this point of the procedure, where a first veno-ventricular passageway has been formed, a plug may be deployed into the cardiac vein, to segregate a portion of the vein. Alternatively, no plug may be deployed, in which case a second veno-ventricular passageway may be formed having an outlet into the same cardiac vein. Device 40 is therefore again inserted along guide wire 101 to a location in the same or a different cardiac vein (or portion of the coronary sinus) proximal of the first passageway, and guidewire 46 is again deployed to puncture the vessel wall and enter the left ventricle. Device 40 is withdrawn, and device 60 and one or more devices 50 are deployed to cut a veno-ventricular passageway of suitable dimensions. At the completion of this step, a number of passageways are formed between the left ventricle, and the overlying portion of the coronary sinus and cardiac veins.

In the event that the clinician desires to further regulate flow through one or more of the veno-ventricular passageways, stent 70 or 70' (or the above-described coil sheet stent) may be deployed in the passageway (see stent 17 in FIG. 4). As described hereinabove, aperture 78 may be selected to limit the flow through stent 70', thereby ensuring that the selected pressure-related parameter does not exceed the predetermined level. Alternatively, if a coiled sheet stent is employed, the stent may be expanded, using a balloon dilatation catheter translated along guidewire 46, so that flow through the passageway is regulated by the degree of radial expansion of the stent.

Referring now to FIG. 10C, after one or more passageways or conduits are formed between the coronary g-sinus or cardiac veins and the left ventricle, plug 92, such as described with respect to FIGS. 5A to 5E, is deployed in the coronary sinus adjacent to the coronary ostium to partially or fully occlude the coronary ostium. Applicants expect that formation of this blockage will raise the overall pressure in the venous system sufficiently so that blood entering the venous system through the veno-ventricular passageways will flow in a retrograde direction. Alternatively, if cardiac veins are segmented by placement of multiple plugs along the length of the vein, applicants expect that little or no blockage of the coronary ostium may be required.

In FIG. 10C, deployment of plug 92 (similar to plug 30 of FIG. 5D) using device 80 of FIG. 9C is described. Device 80 is loaded with plug 92 and advanced along guidewire 101 so that the plug enters through the coronary ostium and engages the interior wall of the coronary sinus. Pusher member 82 is advanced to implant plug 92 into the coronary sinus through the coronary ostium, so that the flange of the plug contacts the endocardium of right atrium RA. Guidewire 101 and device 80 are then withdrawn, completing the procedure.

Applicants expect that a heart treated as described hereinabove can sustain long-term retrograde perfusion of the myocardium using the cardiac venous system. In addition, it is expected that the blockages within the veins and/or coronary sinus will cause a redistribution of flow within the venous system so that a greater fraction of deoxygenated blood exits via the lymphatic system and the Thebesian veins. And because the sizes of the veno-ventricular passageways are dimensioned, and the degree of occlusion of the coronary ostium selected, so that a parameter associated with the pressure in the venous system does not exceed a predetermined value, it is expected that problems associated with edema of the cardiac veins observed in the aforementioned historical attempts at coronary venous bypass grafting will be overcome.

Applicants further note that while the venous system is not co-extensive with the coronary arteries (particularly with respect to the right ventricle), it is nevertheless expected that the apparatus of the present invention, when used in accordance with the exemplary methods described hereinabove, will provide relief in the majority of cases, since right ventricular infarcts are less common.

As will be apparent to one of skill in the art of cardiology, the above described apparatus may be employed in conjunction with other instruments and techniques which are per se known. For example, conventional angiographic methods may be employed to map the arterial and venous systems and the anatomy of the left ventricle. In addition, access to the coronary sinus may be had via the femoral veins. Moreover, passageways between the left ventricle and the coronary sinus or cardiac veins may be created by advancing device 50 (or other suitable cutting instrument) from within the left ventricle. along the portion of guidewire 46 brought out using a snare, for example, by insertion through a femoral artery, the aorta, and through the aortic valve.

Figure 11:
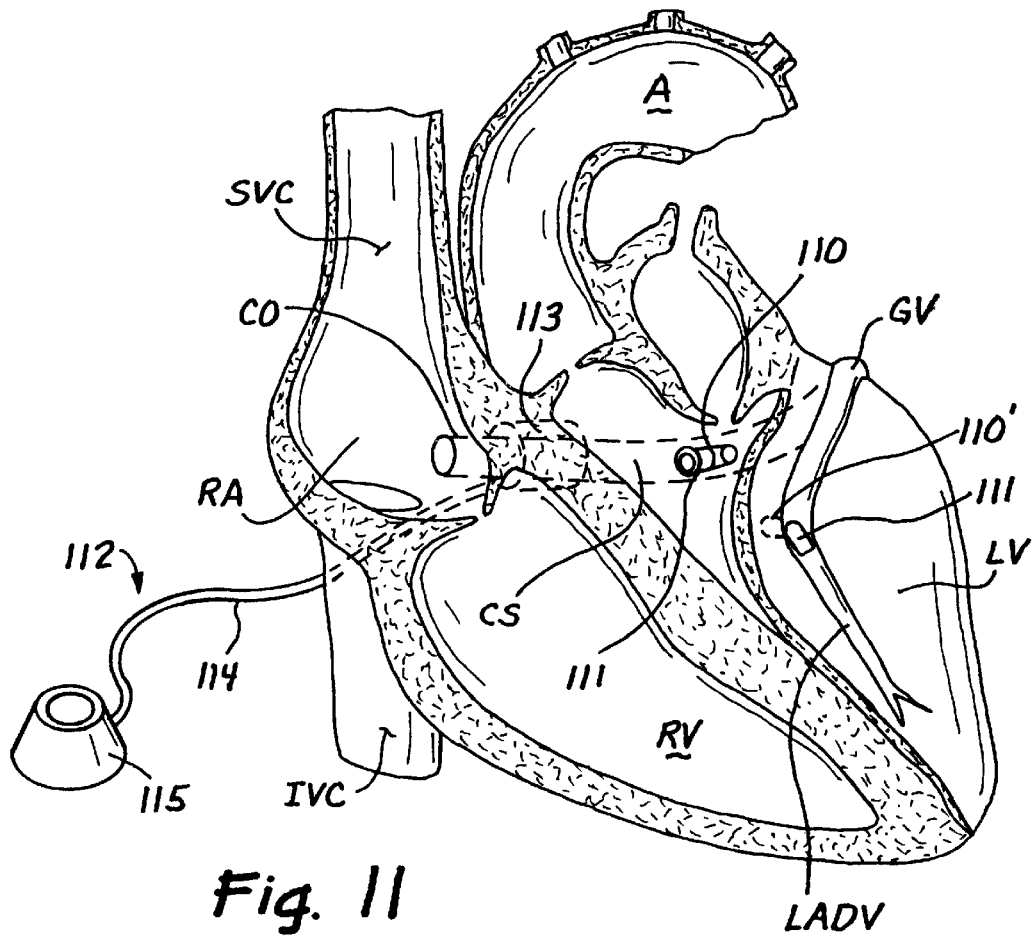
FIG. 11 is a sectional view of a human heart showing the placement of a second embodiment of apparatus constructed in accordance with the present invention.

Referring now to FIG. 11, a heart illustrating use and deployment of a second embodiment of the apparatus of the present invention, suitable for use in an intraoperative method of deployment, is described. Heart H includes veno-ventricular passageway 110 formed between the left ventricle and coronary sinus CS and passageway 110' formed between the left ventricle and left anterior descending vein LADV. Each of passageways 110 and 110' is fitted with a tubular member 111, which maintains the patency of its respective veno-ventricular passageway. Heart H also has affixed to it flow regulator 112, which comprises cuff 113 coupled by lumen 114 to port 115. Cuff 113 is disposed surrounding the coronary sinus in the vicinity of the coronary ostium, while port 115 is disposed subcutaneously in the region of the sternum. Cuff 113 includes inflatable member 116. The inflatable member is actuated by injection of an inflation medium into port 115, and locally constricts the coronary sinus, thereby regulating the volume of blood flowing from the coronary sinus into the right atrium.

Figure 12A:
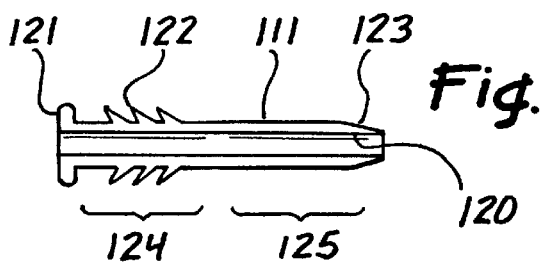

As shown in FIG. 12A, tubular member 111 comprises a length of biocompatible flexible hose, e.g., polyethylene tubing, having central lumen 120, distal flange 121, a region of ribs or barbs 122 that engage the myocardium, and tapered proximal region 123. When deployed in the heart, region 124 is disposed in a passageway cut through the myocardium so that flange 121 abuts against the left ventricular endocardium and barbs or ribs 122 engage the myocardium. Proximal region 125 extends through the epicardium and is bent to approximately a 90° angle to fit within a length of a cardiac vein. Thus, blood ejected from the left ventricle passes through central lumen 120 of tubular member 111 and is directed to flow in a retrograde fashion through the cardiac vein in which the tubular member is disposed. Distal region 124 of tubular member preferably has adequate diametral strength to prevent collapse during contraction of the myocardium, while having sufficient longitudinal flexibility to permit the proximal region to be bent to accommodate the cardiac vein.

Figure 12B:
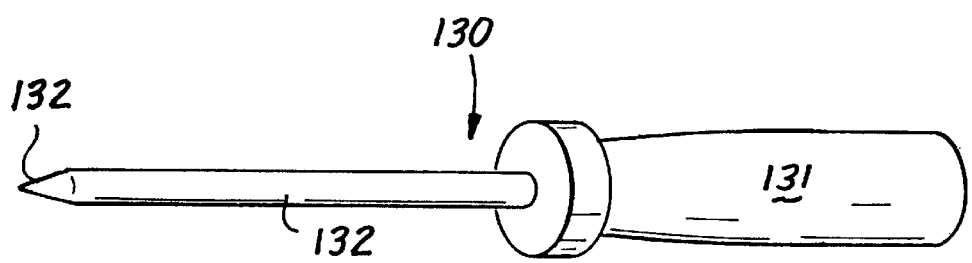

Referring to FIGS. 12B and 12C, apparatus constructed in accordance with the present invention for intraoperatively forming a veno-ventricular passageway and deploying tubular member 111 of FIG. 12A are described. In FIG. 12B awl-type device 130 comprises handle 131 carrying rigid elongated shaft 132 and-sharpened tip 133. Device 130 is employed during an intraoperative procedure, such as the method described hereinbelow, to puncture the proximal and distal walls of a cardiac vein and the underlying myocardium to form a veno-ventricular passageway. Alternatively, device 130 may take the form of a cutting cannula, that cuts and extracts a core of myocardium to create the veno-ventricular passageway.

With respect to FIG. 12B, syringe-type device 135 for deploying tubular member 111 is described. Device 135 includes chamber 136 that accepts tubular member 111 and plunger 137 disposed in chamber 136. Tubular member 111 is disposed in chamber 136 so that flange 121 is approximately aligned with the longitudinal axis of the chamber. Plunger 137 is arranged for reciprocation through chamber 136 to eject the tubular member into the veno-ventricular passageway formed by device 130.

Referring to FIG. 13, flow regulator 112 is described in greater detail. Cuff 113 preferably comprises a rigid material, such as a biocompatible plastic, and encloses inflatable member 116, formed, for example, from polyvinyl chloride or polyethylene. Inflatable member 116 is in fluid communication via lumen 114 to port 115. Lumen 114 preferably comprises a material having low compliance, so that when inflation medium is injected into port 115, the additional inflation medium primarily causes expansion of the inflatable member. Port 115 includes a chamber having self-sealing membrane 117, for example, silicon, that permits an inflation medium to be injected into the port using a conventional non-coring needle. Port 115 also preferably includes a sewing ring for fastening the port in a desired location, e.g., near the sternum. Flow regulator 112 is similar in design and function to the devices described in U.S. Pat. Nos. 3,730,186 and 3,831,583, both to Edmunds et al.

Referring now to FIGS. 14A–14D, a method of the present invention of employing the apparatus of FIGS. 12A–C and 13 is described. A thoracotomy is first performed to expose the mediastinum and the heart. The surgeon then locates a cardiac vein CV through which it is desired to establish retrograde flow. As shown in FIG. 14A, the surgeon then uses device 130 to puncture a passageway through the proximal and distal walls of cardiac vein CV, through the myocardium, and into the left ventricle. Device 130 is then withdrawn. Angled forceps, or a similar type instrument, may be employed to apply pressure to stabilize a portion of the beating heart during the foregoing and subsequent steps. Alternatively, the patient's heart may be stopped and the patient may be put on cardiopulmonary bypass.

Using device 135, in which a tubular member 111 has been loaded, the surgeon inserts the distal end of device 135 into the passageway formed by device 130. Plunger 137 is actuated to eject flange 121 of tubular member 111 into the left ventricle. Device 135 is then withdrawn, leaving tubular member 111 engaged in the myocardium with proximal region 125 projecting through the puncture in the proximal wall of the cardiac vein, as depicted in FIG. 14B.

The surgeon then manipulates proximal region 125 of tubular member 111, either by hand or using a forceps, to bend the tubular member to direct the outlet into the cardiac vein to induce retrograde flow. It is contemplated that a lateral incision may be required to enable the cardiac vein to accept the proximal region of tubular member 111. Upon completion of this step, shown in FIG. 14C, the entry wound in the proximal wall of the cardiac vein, and any lateral incisions required to bend proximal region 125 into the cardiac vein, are closed by sutures 138 using conventional techniques.

The surgeon then implants cuff 113 of flow regulator 112 of FIG. 13 on the coronary sinus in the vicinity of the coronary ostium, and implants port 115 of the device subcutaneously in the region of the sternum. Once the implantation of flow regulator 112 is completed, inflatable member 116 of flow regulator is inflated to create an initial degree of constriction of the coronary sinus. Over a course of time, e.g., several hours, days or longer, the degree of constriction of the coronary sinus may be increased via progressive inflation of inflatable member 116, thereby reducing the flow of blood from the coronary sinus into the right atrium. The coronary sinus therefore may be gradually partially or completely occluded. This, in turn, will cause the blood ejected through tubular members 111 to induce retrograde flow through a progressively larger portion-of the coronary venous system, while allowing the venous system to gradually accommodate the retrograde flow.

Alternatively, instead of implanting flow regulator 112, any of the devices described hereinabove with respect to FIGS. 5A–5E may be implanted in the coronary ostium to achieve a preselected degree of occlusion of the coronary ostium.

Figure 15:
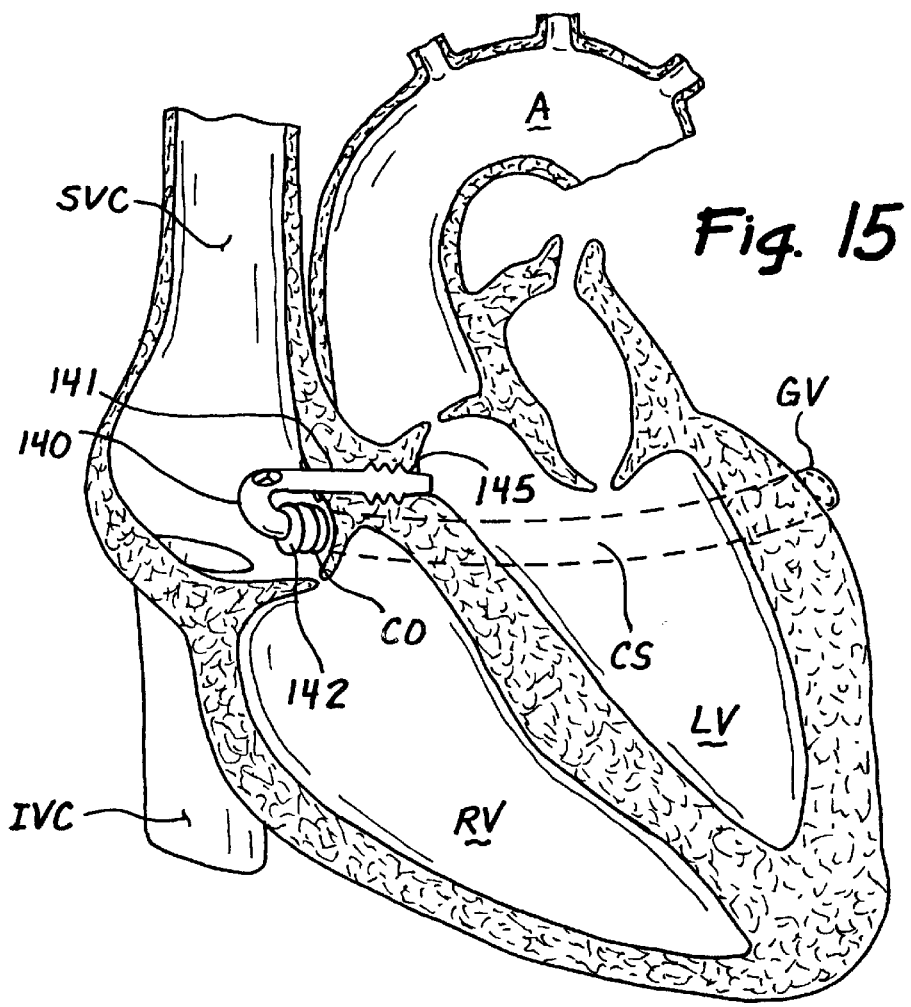
FIG. 15 is a sectional view of a human heart showing the placement of apparatus constructed in accordance with a third embodiment of the present invention.

Referring now to FIG. 15, a third embodiment of the apparatus of the present invention is described, in which like parts of the heart are labeled with like reference numerals. In FIG. 15, a first end 141 of conduit 140 is placed in passageway 145 created between right atrium RA and the posterior septal endocardium of left ventricle LV, while second end 142 of conduit 140 extends through coronary ostium CO and engages the interior wall of coronary sinus CS.

Figure 16:
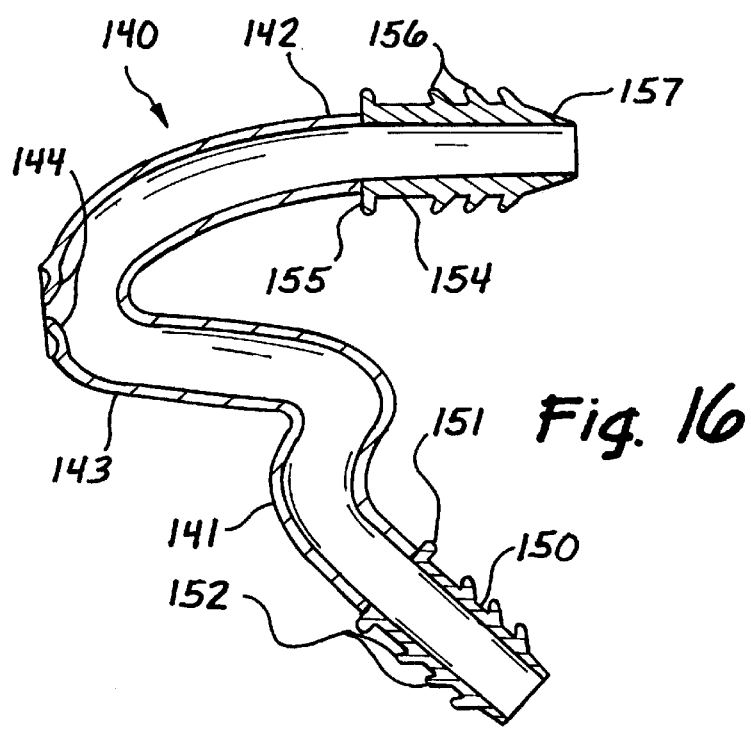
FIG. 16 is a sectional view of the apparatus of FIG. 15 for forming a conduit between the left ventricle and the coronary sinus.

Conduit 140, shown in FIG. 16, has first end 141, second end 142 and midregion 143, which may optionally include valve 144. Conduit 140 may be formed of a flexible and compliant material, such as silicon tubing, or a suitable synthetic graft material, for example, a polyester fabric, such as Dacron®, a registered trademark of E.I. DuPont de Nemours, Wilmington, Del. The material selected for conduit 140 may vary depending upon the intended method of implantation of the conduit. For example, if conduit 140 is to be implanted surgically, there may be advantages to employing a material such as silicon tubing for the conduit. Alternatively, if conduit 140 is to be implanted percutaneously, it may be advantageous to employ a material such as a biocompatible fabric that can be compressed to a smaller diameter to pass through a catheter.

First end 141 of conduit 140 has disposed from it tubular member 150 similar in construction to stent 70 of FIG. 9A. Tubular member 150, which may comprise a compliant material as described hereinabove with respect to stent 70, includes proximal flange 151 and a plurality of ribs or barbs 152 that engage the myocardium and prevent movement of first end 141 when it is implanted. Tubular member 150 may optionally include a one-way valve (not shown) to prevent suction of blood from conduit 140 into the left ventricle.

Second end 142 of conduit 140 includes tubular member 154 having proximal flange 155, a plurality of outwardly extending barbs or ribs 156, and tapered distal portion 157. When implanted in the heart, tapered portion 157 of tubular member 154 extends through the coronary ostium into the coronary sinus, while flange 155 abuts against the right atrial endocardium.

Still referring to FIG. 16, conduit 140 may include valve 144, which may be disposed between first and second ends 141 and 142 of conduit 140, so as to not interfere with implantation of either tubular member 150 or 154. Valve 144 serves the same function in the present embodiment as valve 76 and aperture 78 serve in the embodiments of FIGS. 9A and 9B. For example, valve 144 may be constructed to open when the pressure in conduit 140 exceeds a predetermined value, such as 60 mm Hg. Alternatively, the pressure within conduit 140 may be controlled by the size and taper of the inlet and outlets in tubular members 150 and 154.

As will be apparent from the design of conduit 140 and the description hereinabove, conduit 140 provides retroperfusion of the myocardium via the coronary sinus when implanted. During contraction of the left ventricle, blood in the left ventricle is ejected through tubular member 150, through conduit 140, and into coronary sinus CS via the outlet in tubular member 154. Valve 144, if present, may be constructed to open at a predetermined pressure to vent blood from the left ventricle into the right atrium, or may provide a fixed diameter aperture that reduces the pressure rise in the coronary sinus. Applicants expect that this aspect of the present invention will provide improved myocardium perfusion without the problems encountered in earlier attempts to provide transvenous myocardial perfusion.

Conduit 140 of FIGS. 15 and 16 may be surgically implanted in the heart using method described hereinafter. In particular, following a conventional thoracotomy to expose the heart, an incision may be made through the exterior wall of right atrium RA. A passageway is formed between right atrium RA and the posterior septal endocardium of left ventricle LV via the posterior pyramidal space using a cannulating needle. Tubular member 150 is then implanted in the passageway. Second end 154 of conduit is implanted in coronary ostium CO so that tapered end 157 extends into the coronary sinus and flange 155 abuts against the right atrial endocardium.

Alternatively, conduit 140 may be implanted using a percutaneous approach that is a variation of the Brockenbrough method of catheterizing the left ventricle. The conventional Brockenbrough technique is described in CARDIAC CATHETERIZATION AND ANGIOGRAPHY, W. Grossman, ed., at pages 63–69, published by Lea & Febiger, Philadelphia (1980), which is incorporated herein by reference. In the conventional Brockenbrough technique, a catheter and needle combination is advanced through the right femoral artery and into the right atrium. The needle is then used to puncture the septum between the right and left atria, after which the catheter is advanced through the mitral valve and into the left ventricle.

A method of implanting the apparatus of FIG. 16 is now described using a Brockenbrough needle kit, available from United States Catheter and Instrument Corp., Billerica, Mass. In particular, a Brockenbrough needle is advanced over a guidewire into the right atrium via the right internal jugular vein using standard Seldinger technique. The Brockenbrough needle is then advanced through the right atrial endocardium, the posterior pyramidal space, and through the septal endocardium of the left ventricle to form a passageway between the right atrium and the septal endocardium of the left ventricle. The initial transseptal puncture made with the Brockenbrough needle is dilated using, for example, progressively larger catheters, which are then withdrawn, leaving the guidewire in place.

Figure 17A:
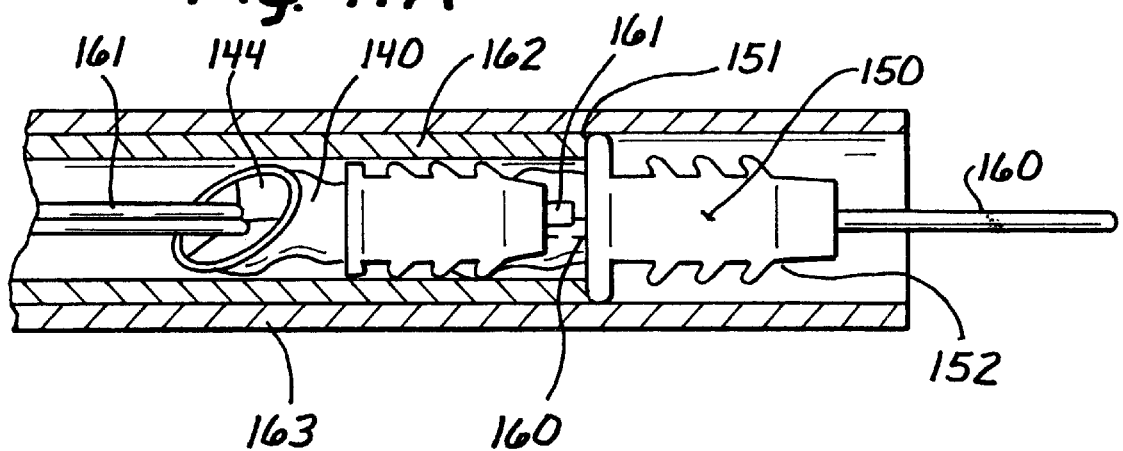
FIGS. 17A and 17B are, respectively, an illustrative sectional view of apparatus for implanting the conduit of FIG. 15, and a side view of a step of percutaneously implanting the apparatus of FIG. 16.

Referring now to FIG. 17A, conduit 140 is threaded onto the proximal end of guidewire 160 that is positioned in the transeptal passageway. Conduit 140 is placed on guidewire 160 so that the guidewire enters the conduit through valve 144 (or if no valve is provided, through a self-sealing silicon membrane) and extends through tubular member 150. Conduit 140 is folded over so that second guidewire 161 extends through valve 144 (or membrane) and tubular member 154. Pusher member 162 is disposed around conduit 140 so that it contacts the proximal face of flange 151, the remainder of conduit 140, including tubular member 154 and valve 144 (or membrane), being inserted within a lumen of pusher member 162. Pusher member 162 and conduit 140 are then loaded into exterior sheath 163. Using this arrangement, pusher member 162 is disposed to push tubular member 150 (and connected conduit 140) in a distal direction along guidewire 160.

Figure 17B:
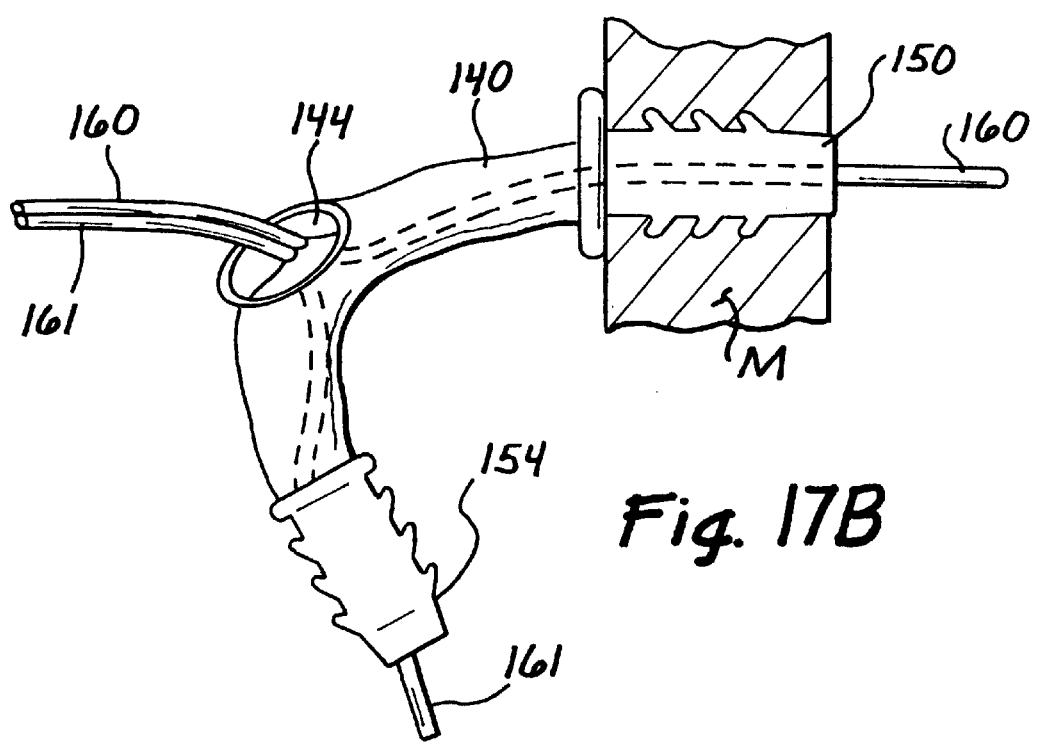

Conduit 140, pusher member 162 and exterior sheath 163 are then advanced along guidewire 160 until the distal end of exterior sheath 163 abuts against the right atrial septum adjacent the transeptal passageway. Pusher member 162 is advanced within exterior sheath 163 to drive tubular member 150 into the transeptal passageway. The plurality of barbs or ribs 152 thereby engage septal myocardium M, while the distal face of flange 151 abuts against the right atrial endocardium, as shown in FIG. 17B. Exterior sheath 163 and pusher member 162 are withdrawn along guidewire 160, leaving the guidewires 160 and 161 in place. When pusher member 162 is withdrawn, conduit 140 and tubular member 154 are deployed, with guidewire 161 already extending from the distal end of tubular member 154. Guidewire 160 is then withdrawn.

Figure 18:
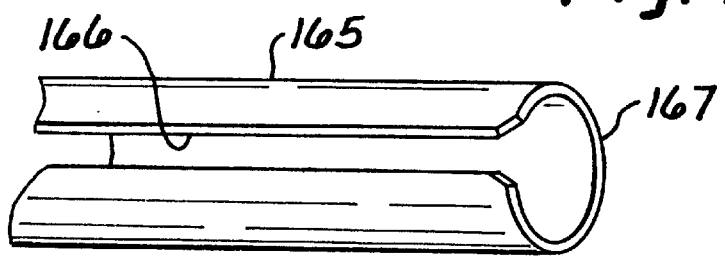
FIG. 18 is a partial perspective of a catheter for implanting a second end of the conduit of FIG. 16.

Referring now to FIG. 18,. catheter 165 having slot 166 in its distal end is employed as will now be described. After deployment of conduit 140 and tubular member 154 from within pusher member 162, guidewire 161 is manipulated so that it enters the coronary sinus through the coronary ostium. Catheter 165 is then advanced along guidewire 161. Slot 166 in catheter 165 is sized to permit conduit 140 to slide within catheter 165 through slot 166, so that distal end face 167 abuts directly against the proximal face of flange 155. Once catheter 165 contacts flange 155 of tubular member 154, catheter 165 is further advanced along guidewire 161 to drive the tapered end of tubular member 154 through the coronary ostium and into engagement with the interior wall of the coronary sinus. Catheter 165 and guidewire 161 are then withdrawn, completing the implantation of no conduit 140.

As will of course be apparent to one of skill in the art, the above method is exemplary only, and other methods may be used to percutaneously implant conduit 140. For example, instead of catheter 165, the grasping teeth of a myocardial biopsy catheter may be used to grasp tubular member 154 and steer the tubular member into engagement with the coronary ostium. Additionally, a second biopsy catheter could be brought into the right atrium via the right femoral artery, if desired, to assist in implantation of either or both ends of conduit 140.

Figure 19:
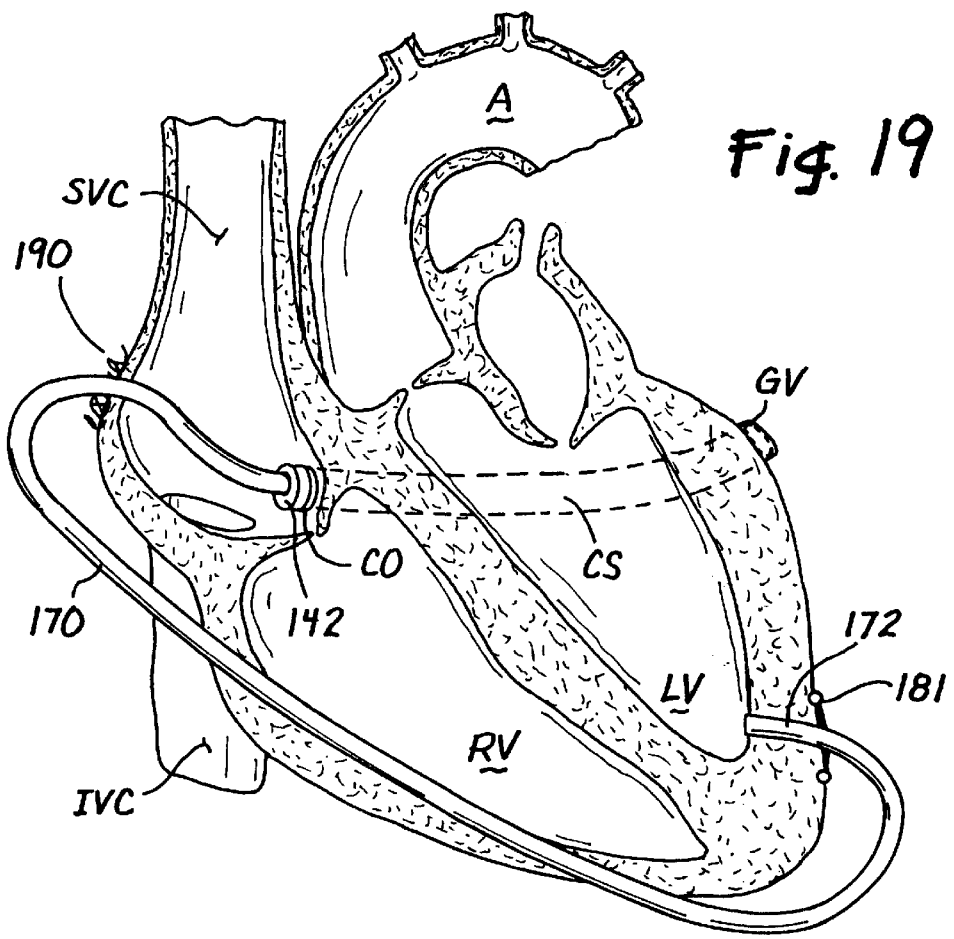
FIG. 19 is a sectional view of a human heart showing the placement of a fourth embodiment of apparatus constructed in accordance with the present invention.
Figure 20:
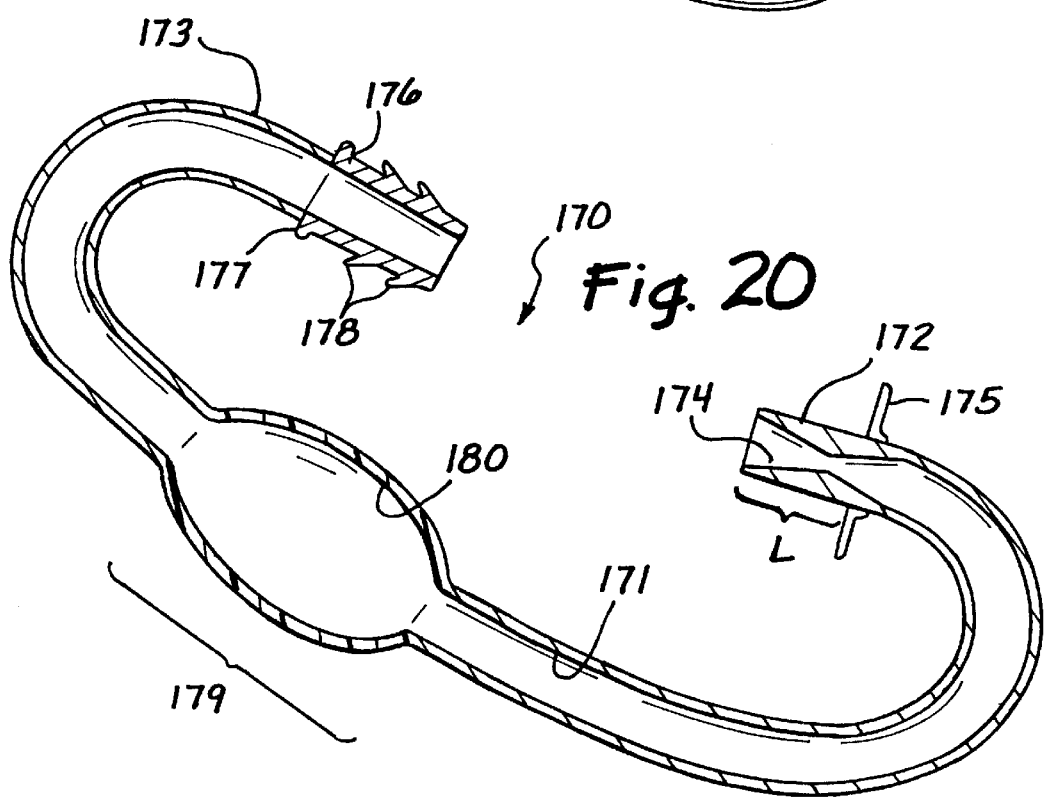
FIG. 20 is a sectional view of the apparatus of depicted in FIG. 19 for forming a conduit between the left ventricle and coronary sinus.

Referring now to FIGS. 19 and 20, a fourth embodiment of the apparatus of the present invention is described. Like the embodiment of FIG. 16, conduit 170 comprises a length of tubing (e.g., polyethylene tubing or graft fabric) that, when implanted, carries oxygenated blood from the left ventricle and into the coronary venous vasculature. Conduit 170 comprises lumen 171, inlet end 172 and outlet end 173.

Inlet end 172 preferably includes tapered tubular bore 174 and sewing ring 175. Tubular bore 174 includes length L that extends into the myocardium when implanted near the apex of the left ventricle. Sewing ring 175 provides means for affixing conduit 170 to the epicardium using for, example, sutures 181, as shown in FIG. 19. Tapered bore 174 is preferably dimensioned to regulate the flow of blood from the left ventricle into the lumen 171. It is expected that the volume of blood flowing into conduit 170 may be effected by the degree of constriction imposed by the taper.

Outlet end 173 includes tubular member 176 similar to that of the embodiment of FIG. 16, and includes flange 177 and ribs or barbs 178 that engage the coronary ostium. Outlet end 173 is implanted (using, for example, forceps) in the coronary ostium through an incision in the right atrium or superior vena cava. Outlet end 173 of conduit 170 thereby achieves a preselected degree of occlusion of the coronary ostium CO, by either partially or fully blocking the outlet of the coronary sinus into the right atrium. Alternatively, tubular member 176 on outlet end 173 may be omitted and the outlet end grafted directly to the coronary sinus CS or great cardiac vein GCV using a conventional purse-string type anastomosis. In this alternative embodiment, the coronary ostium may be partially or fully occluded using any of the devices of FIGS. 5A to 5E or FIG. 13.

In accordance with the pressure regulating aspect of the invention, intermediate region 179 of conduit 170 may optionally include an elastically expandable or compliant portion 180, e.g., comprising latex or a similar elastomeric material. Compliant portion 180 assists in regulating the pressures attained in conduit 170 by elastically swelling and contracting with the blood flow. Compliant portion 180 preferably swells and contracts as a result of the surge in blood pressure during the cardiac cycle, and may be effective in reducing the peak pressure of the blood delivered into the coronary venous vasculature. Alternatively, conduit 170 may include a valve positioned adjacent to outlet end 173 (similar to valve 144 of the embodiment of FIG. 16), to vent excess blood into the right atrium.

As a further alternative embodiment, conduit 170 may include a manifold that connects inlet end 172 to a plurality of outlet ends. Each outlet end may then be anastomosed to a different segment of the cardiac venous vasculature. In this alternative embodiment, the coronary ostium is again preferably fully or partially occluded using any of the devices discussed hereinabove with respect to FIGS. 5A to 5E or FIG. 13.

A method of implanting the conduit of FIG. 20 is now described. First, a cutting cannula having a bore slightly smaller than the diameter of length L of inlet end 172 of conduit 170 is employed to create a transmural passageway in the left ventricle near the apex of the heart (extending through the myocardium from the endocardium to the epicardium). Inlet end 70 is then inserted into the passageway, and sutures are applied to sewing ring 175 to anastomose the inlet end of conduit 170 to the heart. Locking forceps may be applied to collapse the conduit and prevent loss of blood while outlet end 173 is being implanted. In addition, a biocompatible hydrogel may be disposed between the sewing ring and the epicardium to reduce blood loss during the suturing process.

An incision is then made in the superior vena cava or right atrium, and tubular member 176 of outlet end 173 is implanted in the coronary ostium. A purse-string suture 190 is applied where conduit 170 enters the superior vena cava or right atrium to close the entry wound. Thus, blood ejected into conduit 170 through inlet end 172 disposed in the transmural passageway is routed via conduit 170 into the coronary venous system to provide retrograde perfusion of the myocardium.

As will of course be apparent to one of skill in the art, the above described exemplary applications of the apparatus of the present invention are illustrative only, and various of the above-described devices may advantageously be used in combinations other than those recited above.

While preferred illustrative embodiments of the invention are described above, it will be obvious to one skilled in the art that various changes and modifications may be made therein without departing from the invention and the appended claims are intended to cover all such changes and modifications which fall within the true spirit and scope of the invention.

What is claimed is:

1. Apparatus for use in treating ischemic myocardium of a human or animal patient by providing retrograde transvenous myocardial perfusion, the apparatus comprising a kit including:
   a device for forming a passageway, substantially within the patient's myocardium between the left ventricle and venous vasculature:
   a conduit adapted to be transluminally disposed substantially within the passageway formed between a patient's left ventricle and the patient's venous vasculature, the conduit having an outlet in the patient's venous vasculature, the conduit adapted to channel a volume of blood from the left ventricle to the venous vasculature;
   means for achieving a preselected degree of occlusion of the patient's venous vasculature proximal of the outlet to direct the volume of blood to the ischemic myocardium; and,
   means for limiting the peak pressure attained in the patient's venous vasculature to less than 60 mm Hg.

2. The apparatus as defined in claim 1 further comprising:
   a cutting instrument for boring a transmural passageway through the myocardium between the left ventricle and a selected portion of the patient's venous vasculature.

3. The apparatus as defined in claim 2 wherein the cutting instrument is adapted for insertion into the coronary sinus via the coronary ostium, the cutting instrument comprising:

a catheter having a distal end, and a lumen that accepts a guidewire; and a sharpened tubular member disposed on the distal end of the catheter.

4. The apparatus as defined in claim 2 wherein the cutting instrument forms a transmural passageway having a predetermined cross-sectional area.

5. The apparatus as defined in claim 2 wherein the conduit comprises a lumen defined by tissue surrounding the transmural passageway.

6. The apparatus as defined in claim 1 wherein the means for achieving a preselected degree of occlusion also limits a parameter related to the pressure attained in the patient's venous vasculature.

7. The apparatus as defined in claim 1 wherein the conduit comprises:

a tubular member having a bore, an exterior surface, and a plurality of engagement means located on the exterior surface.

8. The apparatus as defined in claim 7 wherein the tubular member further comprises means for regulating flow of blood through the tubular member.

9. The apparatus as defined in claim 8 wherein the means for regulating comprises a one-way valve that prevents backflow of blood from the coronary sinus to the left ventricle.

10. The apparatus as defined in claim 8 wherein the means for regulating comprises a constriction in the bore.

11. The apparatus as defined in claim 1 wherein the means for achieving a preselected degree of occlusion comprises a valve that limits a peak pressure attained within the coronary sinus by venting blood from the coronary sinus into the patient's right atrium when the pressure attained within the coronary sinus exceeds a predetermined value.

12. The apparatus as defined in claim 1 wherein the means for achieving a preselected degree of occlusion comprises:

a woven mesh having a delivery configuration, wherein the woven mesh is longitudinally stretched to a radially contracted position, and a deployed configuration, wherein the woven mesh is released from longitudinal restraint and radially expands;

a biocompatible coating disposed on the woven mesh; and means for forming a constriction in a midregion of the woven mesh.

13. The apparatus as defined in claim 1 wherein the means for achieving a preselected degree of occlusion comprises a plug of open-cell foam having high durometer.

14. The apparatus as defined in claim 1 wherein the means for achieving a preselected degree of occlusion comprises:

a deformable tubular member having a delivery diameter for transluminal delivery, and an expanded diameter, wherein the tubular member is deformably expanded by internal application of a radially outwardly directed force; and a layer of open-cell foam affixed to an exterior surface of the deformable tubular member.

15. A method of providing retrograde transvenous myocardial perfusion to treat ischemic myocardium, the method comprising:

forming a conduit between a patient's left ventricle and the patient's venous vasculature, the conduit having an outlet in the patient's venous vasculature, the conduit channeling blood from the left ventricle to the venous vasculature; and at least partially occluding the patient's venous vasculature proximally of the outlet to direct retrograde blood flow to the ischemic myocardium.

16. The method as defined in claim 15 further comprising regulating a parameter related to the pressure attained in the patient's venous vasculature.

17. The method as defined in claim 16 wherein regulating a parameter comprises placing a constriction in the conduit.

18. The method as defined in claim 16 further comprising periodically adjusting the a degree of occlusion of the patient's venous vasculature.

19. The method as defined in claim 16 wherein regulating a parameter comprises limiting a peak pressure attained in the patient's venous vasculature to a value less than 60 mm Hg.

20. The method as defined in claim 19 wherein limiting a peak pressure comprises venting blood from the coronary sinus into the patient's right atrium when the pressure attained within the coronary sinus exceeds 60 mm Hg.

21. The method as defined in claim 15 wherein forming a conduit comprises:

providing a cutting instrument; and manipulating the cutting instrument to bore a transmural passageway through the myocardium between the left ventricle and a selected portion of the patient's venous vasculature.

22. The method as defined in claim 21 wherein manipulating the cutting instrument comprises positioning the cutting instrument at a desired location by inserting the cutting instrument through the coronary ostium and into the coronary sinus.

23. The method as defined in claim 15 wherein forming a conduit forms a transmural passageway having a predetermined cross-sectional area.

24. The method as defined in claim 15 wherein the conduit comprises a flexible member having a first end, a second end, and a lumen extending therebetween, and forming a conduit comprises:

engaging the first end of the flexible member in fluid communication with the left ventricle; and engaging the second end of the flexible member in the coronary ostium.

25. The method as defined in claim 24 further comprising positioning the conduit within a passageway extending from the right atrial endocardium to the left ventricular septal endocardium.

26. The method as defined in claim 24 wherein engaging the first end of the flexible member in fluid communication with the left ventricle comprises suturing a sewing ring to the epicardium.

* * * * *